United States Patent
Pistorio et al.

(10) Patent No.: US 10,888,504 B2
(45) Date of Patent: *Jan. 12, 2021

(54) HAIR STYLING COMPOSITIONS CONTAINING AQUEOUS WAX DISPERSIONS

(71) Applicant: L'OREAL, Paris (FR)

(72) Inventors: Bradford Joseph Pistorio, Tokyo (JP); Jean-Thierry Simonnet, Rueil Malmasion (FR); Jim Mitchell Singer, South Orange, NJ (US); Henri Samain, Bievres (FR)

(73) Assignee: L'OREAL, Paris (FR)

( * ) Notice: Subject to any disclaimer, the term of this patent is extended or adjusted under 35 U.S.C. 154(b) by 102 days.

This patent is subject to a terminal disclaimer.

(21) Appl. No.: 14/809,321

(22) Filed: Jul. 27, 2015

(65) Prior Publication Data

US 2016/0346172 A1 Dec. 1, 2016

Related U.S. Application Data

(63) Continuation of application No. 13/651,710, filed on Oct. 15, 2012, now Pat. No. 9,408,785.

(51) Int. Cl.

| | | |
|---|---|---|
| *A61Q 5/06* | (2006.01) | |
| *A61K 8/02* | (2006.01) | |
| *A61K 8/04* | (2006.01) | |
| *A61K 8/92* | (2006.01) | |
| *A61K 8/37* | (2006.01) | |
| *A61K 8/81* | (2006.01) | |
| *A61K 8/891* | (2006.01) | |
| *A45D 7/06* | (2006.01) | |
| *A61K 8/41* | (2006.01) | |
| *A61K 8/44* | (2006.01) | |
| *A61K 8/60* | (2006.01) | |
| *A61K 8/86* | (2006.01) | |
| *A61Q 5/12* | (2006.01) | |

(52) U.S. Cl.
CPC .............. *A61K 8/0241* (2013.01); *A45D 7/06* (2013.01); *A61K 8/025* (2013.01); *A61K 8/04* (2013.01); *A61K 8/046* (2013.01); *A61K 8/37* (2013.01); *A61K 8/416* (2013.01); *A61K 8/442* (2013.01); *A61K 8/602* (2013.01); *A61K 8/8147* (2013.01); *A61K 8/8182* (2013.01); *A61K 8/86* (2013.01); *A61K 8/891* (2013.01); *A61K 8/922* (2013.01); *A61K 8/927* (2013.01); *A61Q 5/06* (2013.01); *A61K 2800/412* (2013.01); *A61Q 5/12* (2013.01)

(58) Field of Classification Search
None
See application file for complete search history.

(56) References Cited

U.S. PATENT DOCUMENTS

| | | |
|---|---|---|
| 2,463,264 A | 3/1949 | Graenacher et al. |
| 3,869,454 A | 3/1975 | Lang et al. |
| 3,955,918 A | 5/1976 | Lang |
| 3,985,499 A | 10/1976 | Lang et al. |
| 4,025,301 A | 5/1977 | Lang |
| 4,151,162 A | 4/1979 | Lang et al. |
| 4,861,583 A | 8/1989 | Sramek |
| 5,053,221 A | 10/1991 | Robertson et al. |
| 5,166,355 A | 11/1992 | Leistner et al. |
| 5,237,071 A | 8/1993 | Leistner et al. |
| 5,585,091 A | 12/1996 | Pelzer et al. |
| 5,618,523 A | 4/1997 | Zysman et al. |
| 5,708,151 A | 1/1998 | Mockli |
| 5,773,611 A | 6/1998 | Zysman et al. |
| 5,858,338 A | 1/1999 | Piot et al. |
| 5,874,072 A | 2/1999 | Alwattari et al. |
| 5,925,337 A | 7/1999 | Arraudeau et al. |
| 6,024,948 A | 2/2000 | Samain et al. |
| 6,066,315 A | 5/2000 | Melby et al. |
| 6,066,316 A | 5/2000 | Shiojima et al. |
| 6,093,385 A | 7/2000 | Habeck et al. |
| 6,120,778 A | 9/2000 | Simonnet |
| 6,126,929 A | 10/2000 | Mougin |
| 6,132,736 A * | 10/2000 | Mellul .................. A61K 8/044 424/401 |
| 6,159,455 A | 12/2000 | Habeck et al. |
| 6,165,457 A | 12/2000 | Midha et al. |

(Continued)

FOREIGN PATENT DOCUMENTS

| | | |
|---|---|---|
| CA | 2420675 A1 | 8/2003 |
| DE | 2810130 A1 | 9/1979 |

(Continued)

OTHER PUBLICATIONS

International Search Report and Written Opinion for counterpart Application No. PCT?US2013/060338, dated Dec. 23, 2013.
Wertz, et al., Essential Fatty Acids and Epidermal Integrity, Archive of Dermatology, vol. 123, Oct. 1987, pp. 1381-1384.
Reiger, Martin M. (2000). Harry's Cosmeticology, vols. I-II (8th Edition). Chemical Publishing Company Inc. Online version available at: http://app.knovel.com/hotlink/toc/id:kpHCVIIIEH/harrys-cosmeticology.

(Continued)

*Primary Examiner* — Jyothsna A Venkat
(74) *Attorney, Agent, or Firm* — The Marbury Law Group, PLLC

(57) ABSTRACT

The present invention is directed to a hair styling composition and methods of using the composition, wherein the composition comprises: (a) an aqueous dispersion containing: (i) at least one solid wax particle having a particle size ranging from equal to or greater than 1 micron to about 100 microns and comprising at least one wax having a melting point of greater than 35° C.; (ii) a surfactant mixture comprising at least one nonionic surfactant and at least one ionic surfactant; and (iii) water; and (b) at least one cosmetically acceptable carrier.

30 Claims, 2 Drawing Sheets

(56) References Cited

U.S. PATENT DOCUMENTS

| | | | |
|---|---|---|---|
| 6,191,301 B1 | 2/2001 | Habeck et al. |
| 6,235,271 B1 | 5/2001 | Luther et al. |
| 6,238,649 B1 | 5/2001 | Habeck et al. |
| 6,248,336 B1 | 6/2001 | McDermott |
| 6,274,131 B1 | 8/2001 | Piot et al. |
| 6,316,011 B1 | 11/2001 | Ron et al. |
| 6,326,013 B1 | 12/2001 | Lemann et al. |
| 6,372,201 B1 | 4/2002 | Leuridan et al. |
| 6,436,373 B1 | 8/2002 | Habeck et al. |
| 6,464,990 B2 | 10/2002 | Simonnet et al. |
| 6,503,495 B1 | 1/2003 | Alwattari et al. |
| 6,514,485 B1 | 2/2003 | Malpede et al. |
| 6,605,311 B2 | 8/2003 | Villagran et al. |
| 6,645,476 B1 | 11/2003 | Morschhauser et al. |
| 6,689,855 B2 | 2/2004 | Smith et al. |
| 6,689,856 B2 | 2/2004 | L'Alloret |
| 6,755,202 B1 | 6/2004 | Scholey et al. |
| 6,793,940 B2 | 9/2004 | Tournihac et al. |
| 6,830,670 B1 | 12/2004 | Viovy et al. |
| 6,838,514 B2 | 1/2005 | Yeung et al. |
| 6,870,012 B2 | 3/2005 | Cohn et al. |
| 6,878,754 B2 | 4/2005 | L'Alloret |
| 6,946,123 B2 | 9/2005 | De La Poterie et al. |
| 6,995,209 B2 | 2/2006 | Olivieri et al. |
| 7,008,628 B2 | 3/2006 | Ron et al. |
| 7,029,662 B2 | 4/2006 | Auguste et al. |
| 7,115,255 B2 | 10/2006 | L'Alloret |
| 7,138,110 B2 | 11/2006 | Auguste et al. |
| 7,189,388 B2 | 3/2007 | Auguste et al. |
| 7,211,244 B2 | 5/2007 | Auguste et al. |
| 7,217,752 B2 | 5/2007 | Schmucker-Castner et al. |
| 7,288,575 B2 | 10/2007 | Lannibois-Drean et al. |
| 7,311,736 B2 | 12/2007 | Burgaud et al. |
| 7,335,348 B2 | 2/2008 | Giroud et al. |
| 7,339,013 B2 | 3/2008 | Pagnoux et al. |
| 7,399,320 B2 | 7/2008 | Bugaud et al. |
| 7,431,919 B2 | 10/2008 | Travkina et al. |
| 7,482,419 B2 | 1/2009 | Caprasse et al. |
| 7,722,859 B2 | 5/2010 | L'Alloret |
| 7,772,214 B2 | 8/2010 | Vatter et al. |
| 7,871,600 B2 | 1/2011 | Hiraishi et al. |
| 7,883,690 B2 | 2/2011 | Collin et al. |
| 7,883,692 B2 | 2/2011 | L'Alloret |
| 7,998,465 B2 | 8/2011 | De La Poterie et al. |
| 8,211,415 B2 | 7/2012 | Pays et al. |
| 8,388,940 B2 | 3/2013 | Pastor et al. |
| 8,685,375 B2 | 4/2014 | Arditty et al. |
| 8,920,787 B2 | 12/2014 | Li et al. |
| 9,408,785 B2 * | 8/2016 | Pistorio .................... A61Q 5/06 |
| 2001/0003586 A1 | 6/2001 | Vatter et al. |
| 2002/0001570 A1 | 1/2002 | Heidenfelder et al. |
| 2002/0016310 A1 | 2/2002 | Habeck et al. |
| 2002/0085986 A1 | 7/2002 | De La Poterie et al. |
| 2002/0098217 A1 | 7/2002 | Piot et al. |
| 2002/0198328 A1 | 12/2002 | L'Alloret |
| 2003/0026815 A1 | 2/2003 | Scott et al. |
| 2003/0031640 A9 | 2/2003 | De La Poterie et al. |
| 2003/0039671 A1 | 2/2003 | Tournilhac et al. |
| 2003/0059377 A1 | 3/2003 | Riley |
| 2003/0059388 A1 | 3/2003 | Auguste et al. |
| 2003/0059389 A1 | 3/2003 | Tournilhac et al. |
| 2003/0060559 A1 | 3/2003 | Oliviere et al. |
| 2003/0064045 A1 | 4/2003 | Tournilhac et al. |
| 2003/0092776 A1 | 5/2003 | Ron et al. |
| 2003/0099709 A1 | 5/2003 | Shah et al. |
| 2003/0103915 A1 | 6/2003 | Quintini |
| 2003/0138465 A9 | 7/2003 | Douin et al. |
| 2003/0143168 A1 | 7/2003 | Geffroy |
| 2003/0143180 A1 | 7/2003 | Giroud et al. |
| 2003/0147832 A1 | 8/2003 | L'Alloret |
| 2003/0204014 A1 | 10/2003 | Yeung et al. |
| 2004/0022752 A1 | 2/2004 | De La Poterie |
| 2004/0054076 A1 | 3/2004 | Lannibois-Drean et al. |
| 2004/0091447 A1 * | 5/2004 | Pays .................... A61K 8/86 424/70.22 |
| 2004/0172061 A1 | 9/2004 | Yoshioka et al. |
| 2004/0198904 A1 | 10/2004 | Braun et al. |
| 2004/0214913 A1 | 10/2004 | L'Alloret |
| 2005/0002887 A1 | 1/2005 | Rollat-Corvol et al. |
| 2005/0013782 A1 | 1/2005 | Goppel et al. |
| 2005/0028300 A1 | 2/2005 | Bugaud et al. |
| 2005/0031656 A1 | 2/2005 | Pays et al. |
| 2005/0053567 A1 | 3/2005 | Liu |
| 2005/0112080 A1 | 5/2005 | Cao et al. |
| 2005/0169949 A1 | 8/2005 | De La Poterie et al. |
| 2005/0175573 A1 | 8/2005 | Pagnoux et al. |
| 2005/0191251 A1 | 9/2005 | Kravtchenko et al. |
| 2005/0191258 A1 | 9/2005 | De La Poterie et al. |
| 2005/0228126 A1 | 10/2005 | Lannibois-Drean et al. |
| 2006/0030655 A1 | 2/2006 | L'Alloret et al. |
| 2006/0111518 A1 | 5/2006 | L'Alloret |
| 2006/0130248 A1 * | 6/2006 | Pays .................... A61K 8/8152 8/406 |
| 2006/0156479 A1 | 7/2006 | Hercouet et al. |
| 2006/0189485 A1 * | 8/2006 | Hirokawa ............... A01N 25/14 504/367 |
| 2006/0263438 A1 | 11/2006 | Biatry et al. |
| 2006/0292095 A1 | 12/2006 | Biatry et al. |
| 2007/0106020 A1 | 5/2007 | Braun et al. |
| 2007/0149703 A1 | 6/2007 | Caprasse et al. |
| 2007/0196299 A1 | 8/2007 | Constantinides et al. |
| 2007/0275020 A1 | 11/2007 | Lendlein et al. |
| 2008/0014164 A1 | 1/2008 | Jacquier |
| 2008/0081024 A1 | 4/2008 | Beasley et al. |
| 2008/0092307 A1 | 4/2008 | Burgaud et al. |
| 2008/0138300 A2 * | 6/2008 | Yu .......................... A61K 8/027 424/59 |
| 2008/0311050 A1 | 12/2008 | Lendlein et al. |
| 2009/0061004 A1 | 3/2009 | Birkel et al. |
| 2009/0136439 A1 | 5/2009 | Feng et al. |
| 2009/0142289 A1 | 6/2009 | Arditty et al. |
| 2009/0241980 A1 | 10/2009 | Wyatt et al. |
| 2009/0282623 A1 | 11/2009 | Goget et al. |
| 2009/0298971 A1 * | 12/2009 | Leotsakos ............ C09D 133/08 523/207 |
| 2010/0143424 A1 | 6/2010 | Kanazawa |
| 2010/0150858 A1 | 6/2010 | Runglertkriangkrai |
| 2010/0172853 A1 | 7/2010 | Pavel et al. |
| 2010/0190870 A1 | 7/2010 | L'Alloret |
| 2010/0242984 A1 | 9/2010 | Arditty et al. |
| 2010/0247470 A1 | 9/2010 | Friel et al. |
| 2010/0278770 A1 | 11/2010 | Arditty et al. |
| 2011/0073128 A1 | 3/2011 | Ogawa et al. |
| 2011/0123472 A1 | 5/2011 | Atis |
| 2011/0146702 A1 | 6/2011 | Raineau |
| 2011/0150807 A1 | 6/2011 | Bui et al. |
| 2011/0182839 A1 | 7/2011 | Numata |
| 2011/0236342 A1 | 9/2011 | Dop |
| 2011/0269839 A1 | 11/2011 | Dolatkhani et al. |
| 2012/0070391 A1 | 3/2012 | Schultze et al. |
| 2012/0093560 A1 | 4/2012 | Arditty |
| 2012/0129095 A1 | 5/2012 | Levanon et al. |
| 2013/0112220 A1 | 5/2013 | Kergosien |
| 2014/0013521 A1 | 1/2014 | Goget et al. |
| 2014/0102467 A1 | 4/2014 | Pistorio et al. |
| 2014/0102468 A1 | 4/2014 | Pistorio et al. |
| 2014/0105845 A1 | 4/2014 | Bui et al. |
| 2014/0105942 A1 | 4/2014 | Pistorio et al. |
| 2014/0105943 A1 | 4/2014 | Pistorio et al. |
| 2014/0105944 A1 | 4/2014 | Pistorio et al. |
| 2014/0105945 A1 | 4/2014 | Bui et al. |

FOREIGN PATENT DOCUMENTS

| | | |
|---|---|---|
| DE | 19726184 A1 | 12/1998 |
| DE | 19746654 A1 | 2/1999 |
| DE | 19755649 A1 | 6/1999 |
| DE | 19855649 A1 | 6/2000 |
| DE | 10150726 A1 | 4/2003 |
| DE | 10162844 A1 | 7/2003 |
| EP | 0133981 A2 | 5/1985 |
| EP | 0583814 A1 | 2/1994 |
| EP | 0629649 A1 | 12/1994 |

(56) References Cited

FOREIGN PATENT DOCUMENTS

| | | |
|---|---|---|
| EP | 0669323 A1 | 8/1995 |
| EP | 0692506 A2 | 1/1996 |
| EP | 0714954 A2 | 6/1996 |
| EP | 0832642 A2 | 4/1998 |
| EP | 0893119 A1 | 1/1999 |
| EP | 0966946 A1 | 12/1999 |
| EP | 0967200 A1 | 12/1999 |
| EP | 1008586 A1 | 6/2000 |
| EP | 1027883 A2 | 8/2000 |
| EP | 1112735 A1 | 7/2001 |
| EP | 1133980 A2 | 9/2001 |
| EP | 1174113 A1 | 1/2002 |
| EP | 1269974 A1 | 1/2003 |
| EP | 1300137 A2 | 4/2003 |
| EP | 1378544 A2 | 1/2004 |
| EP | 1407791 A1 | 4/2004 |
| EP | 1466588 A1 | 10/2004 |
| EP | 1674073 A1 | 6/2006 |
| EP | 2008644 A2 | 12/2008 |
| FR | 2140205 A1 | 1/1973 |
| FR | 2189006 A1 | 1/1974 |
| FR | 2285851 A1 | 4/1976 |
| FR | 2673179 A1 | 8/1992 |
| FR | 2694939 A1 | 2/1994 |
| FR | 2788008 A1 | 7/2000 |
| FR | 2811886 A1 | 1/2002 |
| FR | 2820976 A1 | 8/2002 |
| FR | 2840907 A1 | 12/2003 |
| FR | 2844190 A1 | 3/2004 |
| FR | 2856923 A1 | 1/2005 |
| FR | 2940062 A1 | 6/2010 |
| FR | 2961396 A1 | 12/2011 |
| FR | 2975293 A1 | 11/2012 |
| GB | 2206339 A | 1/1989 |
| GB | 2303549 A | 2/1997 |
| GB | 2408510 A | 1/2005 |
| JP | 2003-012478 A | 1/2003 |
| WO | 89/01771 A1 | 3/1989 |
| WO | 89/04653 A1 | 6/1989 |
| WO | 91/12793 A1 | 9/1991 |
| WO | 93/04665 A1 | 3/1993 |
| WO | 95/01772 A1 | 1/1995 |
| WO | 95/15144 A1 | 6/1995 |
| WO | 97/00275 A2 | 1/1997 |
| WO | 98/06438 A1 | 2/1998 |
| WO | 98/29487 A1 | 7/1998 |
| WO | 98/48768 A1 | 11/1998 |
| WO | 98/50005 A1 | 11/1998 |
| WO | 00/00222 A1 | 1/2000 |
| WO | 00/07603 A2 | 2/2000 |
| WO | 00/35961 A1 | 6/2000 |
| WO | 00/38851 A1 | 7/2000 |
| WO | 01/41735 A2 | 6/2001 |
| WO | 09/09064 A1 | 1/2002 |
| WO | 02/15873 A2 | 2/2002 |
| WO | 02/15875 A2 | 2/2002 |
| WO | 02/32560 A2 | 4/2002 |
| WO | 02/076392 A2 | 10/2002 |
| WO | 03/008462 A1 | 1/2003 |
| WO | 03/032930 A1 | 4/2003 |
| WO | 03/106536 A2 | 12/2003 |
| WO | 2004/006872 A1 | 1/2004 |
| WO | 2005/100444 A1 | 10/2005 |
| WO | 2009/026113 A2 | 2/2009 |
| WO | 2011/103080 A1 | 8/2011 |
| WO | 2011/111084 A1 | 9/2011 |
| WO | 2011/125086 A1 | 10/2011 |
| WO | 2012/028456 A2 | 3/2012 |
| WO | 2012/037502 A2 | 3/2012 |
| WO | 2013/131575 A1 | 9/2013 |
| WO | 2013/190136 A2 | 12/2013 |
| WO | 2014/060405 A2 | 4/2014 |

OTHER PUBLICATIONS

Andreas Lendlin and Robert Langer "Biodegradable, Elastic Shape—Memory Polymers for Potential Biomedical Applications"—Sciencemag, May 31, 2002, p. 1673-1676, vol. 296.

Andreas Lendlin, Hongyan Jiang, Oliver Junger, and Robert Langer "Light-induced shape memory polymers"—Nature Publishing Group, Apr. 14, 2005, p. 879-882, vol. 434.

Marc Behl and Andreas Lendlin "Shape memory polymers"—Materials today, Apr. 2007, p. 20-28, vol. 10, No. 4.

K. Robson, M.E Stewart, S. Michelsen, N.D. Lazo, D.T. Downing "6-Hydroxy-4-sphingenine in human epidermal ceramides"—Journal of Lipid Research, p. 2060-2068, vol. 35, 1994.

McCutcheon's "Emulsifiers & Detergents"—McCutcheon's Division, McPublishing Co., 175 Rock Road, Glen Rock, NJ 07452, USA, 1986 North American Edition.

McCutcheon's "vol. 2:Functional Materials"—McCutcheon's Division, The Manufacturing Confectioner Publishing Co., 175 Rock Rd, Glen Rock, NJ 07452, USA, 1992 North American Ed.

Non-Final Office Action for copending U.S. Appl. No. 13/651,732, dated Mar. 25, 2017.

Final Office Action for copending U.S. Appl. No. 13/651,732, dated Nov. 18, 2015.

Non-Final Office Action for copending U.S. Appl. No. 13/651,732, dated Apr. 7, 2016.

Non-Final Office Action for copending U.S. Appl. No. 13/651,768, dated Oct. 6, 2015.

Final Office Action for copending U.S. Appl. No. 13/651,768, dated Mar. 24, 2016.

Non-Final Office Action for copending U.S. Appl. No. 14/251,373, dated Dec. 31, 2015.

Final Office Action for copending U.S. Appl. No. 14/251,373, dated May 5, 2016.

Non-Final Office Action for copending U.S. Appl. No. 14/251,373, dated Apr. 3, 2017.

Final Office Action for copending U.S. Appl. No. 14/251,373, dated Nov. 15, 2017.

Office Action for counterpart European Application No. 13776511.1, dated Jun. 2, 2017.

Non-Final Office Action for co-pending U.S. Appl. No. 14/251,373, dated Mar. 18, 2019.

Non-Final Office Action for co-pending U.S. Appl. No. 13/651,732, dated May 22, 2019.

International Search Report and Written Opinion for PCT/EP2014/054873, dated May 13, 2015.

English language Abstract for FR 2975293A1 (Nov. 23, 2012).

International Preliminary Report on Patentability for PCT/EP2013/071516, dated Apr. 30, 2015.

International Preliminary Report on Patentability for PCT/EP2013/071518, dated Apr. 30, 2015.

* cited by examiner

HAIR STYLING COMPOSITIONS CONTAINING AQUEOUS WAX DISPERSIONS

FIELD OF THE INVENTION

The present invention relates to compositions containing aqueous wax dispersions and methods of using these compositions to shape or position the hair. More particularly, the invention is directed to hair styling compositions containing an aqueous dispersion comprising a solid wax particle, a surfactant mixture comprising a nonionic surfactant and an ionic surfactant, and water.

BACKGROUND OF THE INVENTION

Consumer products such as cosmetics, personal care, and household products, as well as pharmaceutical and industrial products, employ ingredients that allow these products to form a film or coating on various substrates such as keratinous substrates (e.g., hair and skin), hard surfaces (e.g., wood and metal), and other non-keratinous substrates, (e.g., fabrics and articles). Those ingredients which help form a film or coating on the surface of a substrate may be chosen from a variety of raw materials such as waxes, polymers, resins and oils. At the same time, products which employ these ingredients are designed to impart certain desirable properties such as shine, water resistance, transfer resistance, scratch resistance, color and a glazed appearance to a surface.

In particular, waxes are highly desirable in cosmetics and personal care products in order to provide properties such as shine, smoothness, and slipperiness to various types of surfaces, as well as a protective coating against external factors such as exposure to water or moisture and physical rubbing. Also, hair styling products which contain one or more of the above-mentioned ingredients can be used to impart shape or style to the hair and/or to help maintain a particular hair style. These ingredients can also be used to provide a water-resistant film or coating on the hair, and also to help maintain the appearance and condition of hair upon exposure to extreme environmental conditions, for example, high or low humidity, which can cause the hair to become frizzy. In addition, these ingredients can provide structure and texture to the products and a certain feel and texture to the hair.

Nevertheless, consumers continuously seek new hair cosmetic and hair care products with improved performance and therefore, challenges still exist today in terms of optimizing or enhancing the performance of these ingredients in such products. For example, there are numerous hair styling/shaping products on the market such as temporary and permanent styling products. However, the effects of temporary styling products generally last for only a relatively short period of time. Thus, in order to re-shape or re-style the hair, the consumer has to either re-apply a hair styling product and/or wash the hair again followed by a new application of the product and restyling the hair. Permanent styling also has the drawback of having to treat the hair with permanent waving or straightening/relaxing chemical treatments which may damage the hair.

Moreover, the formulation of waxes, polymers, resins and oils in various galenic forms of hair cosmetic products such as sprays, foams, emulsions, gels, mousses, pastes and sticks may pose a challenge since some of these ingredients may not be easily introduced and/or dispersed into these galenic forms. In addition, the final formulas using these ingredients have to remain stable over time.

For example, waxes are traditionally employed in a paste or pomade but may not be easily formulated in a spray or foam product, particularly at a concentration that will be sufficient to impart the desirable attributes obtained from a wax ingredient. The type of wax may also affect the stability and dispersion of the wax particles in the formulation since wax particles could agglomerate. Certain waxes may also result in an undesirable rough texture and/or sticky and tacky feel of the product and/or to the treated substrate. In paste formulas, waxes are first melted and then blended with oils, plasticizers, clays and/or any other additives. In other words, formulating with waxes still poses a challenge with respect to optimizing the benefits that can be obtained from the wax or waxes themselves. Thus, there still exists a need to improve how ingredients such as waxes, polymers, resins and oils can be formulated into various galenic forms, and at the same time, deliver the benefits derived from these ingredients and enhance the performance of other ingredients.

Thus, various technologies directed towards the use of waxes, polymers, resins and oils have been developed. For example, shape memory polymers (SMPs) have been found to have the ability to change shape and therefore, provide certain materials made of such polymers with the ability to change their shapes or revert back to their original shape upon deformation, particularly, when an external stimuli such as heat or light is applied; SMPs may be used in packaging films, fabrics and medical devices (Marc Biehl and Andreas Lendlein (2007). *Shape Memory Polymers, Materials Today.* 10 (4), pp. 20-28). In the area of cosmetics and hair care, US20080311050 and US20070275020 teach the use of shape memory polymers in hair treatment compositions. However, SMPs are typically complex polymer systems which may pose challenges in synthesis procedures and formulation in terms of the choice of solvents and delivery/galenic form.

Other teachings, such as DE2810130, disclose applying a polyamide powder onto hair and heating the hair to bond the hair in a particular style; however, this reference does not teach that the hair can be re-styled or re-positioned and appears to be directed to wigs. WO8904653 and WO8901771 disclose the use of heat-activated hair styling compositions containing water-soluble polyethylene oxide polymers. EP1174113, U.S. Pat. No. 7,998,465 and US20120070391 are directed to the use of specific polymers, including thermofusible polymers, heat-expandable particles comprising certain polymers, and polysiloxanes and silanes. However, the use of polymers may still result in sticky formulas, may be difficult to formulate into a stable dispersion as a result of compatibility issues with surfactants, and do not necessarily provide a long lasting coat or film or the ability to easily re-style or re-position the hair without reapplying a product, for example.

U.S. Pat. Nos. 7,871,600, 6,066,316, JP2003012478, US20060292095 and US20060263438 teach the preparation of wax and oil dispersions in hair cosmetic compositions. For instance, U.S. Pat. No. 7,871,600 teaches the use of a wax dispersion in a hair styling composition. However, said composition additionally requires a styling polymer and a relatively high amount of wax of from 30% to 45% by weight of the composition. U.S. Pat. No. 6,066,316 discloses fine wax dispersions containing wax, an amphoteric surfactant and a nonionic surfactant where the size of the wax particles is about 30 nm and the nonionic surfactant is directed towards a specific class, i.e., polyoxypropylene alkyl ethers. JP2003012478 teaches a hair composition with hair-remodelling properties comprising an oil soluble material, a nonionic surfactant and water; the oil soluble material contains fatty acid, higher alcohol and wax. US20060292095 and US20060263438 disclose dispersions of oil particles calibrated to specific sizes and shapes; these particles are for use in sunscreen and skin care compositions. Nevertheless, the preparation of wax and oil particle dispersions and formulating with these dispersions in various galenic forms may still pose challenges, particularly since there are a number of factors to consider when working with wax and oil particles such as size, shape, hardness and melting point. Another consideration is the challenge of finding a convenient and easy way of optimizing the benefits that are delivered to substrates treated with the compositions containing these dispersions. In particular, many challenges still exist, not only in effectively introducing ingredients into products used to style and shape hair, but also in creating products which provide several benefits to hair while having the appearance and texture that are desirable to the consumer.

Thus, the ability to provide hair styling/shaping products to help maintain the shape of hair or to re-position/re-style the hair without reapplication of product, to provide humidity resistance and impart other desirable properties to hair such as shine, conditioning, softness and combability as well while having good aesthetic features remain as additional areas for improvement, particularly in connection with the use of waxes in such products.

BRIEF SUMMARY OF THE INVENTION

The present invention relates to a hair styling composition comprising:
- (a) an aqueous dispersion containing:
  - (i) at least one solid wax particle having a particle size ranging from equal to or greater than 1 micron to about 100 microns and comprising at least one wax having a melting point of greater than 35° C.;
  - (ii) a surfactant mixture comprising at least one nonionic surfactant and at least one ionic surfactant; and
  - (iii) water; and
- (b) at least one cosmetically acceptable carrier.

The present invention also relates to a method of shaping hair, the method comprising:
- (a) applying onto the hair, a composition containing an aqueous dispersion and a cosmetically acceptable carrier;
  - wherein the aqueous dispersion comprises:
  - (i) at least one solid wax particle having a particle size ranging from equal to or greater than 1 micron to about 100 microns and comprising at least one wax having a having a melting point of greater than 35° C.;
  - (ii) a surfactant mixture comprising at least one nonionic surfactant and at least one ionic surfactant; and
  - (iii) water; and
- (b) heating the hair in order to melt the at least one solid wax particle.

DETAILED DESCRIPTION OF THE INVENTION

Figure 1:
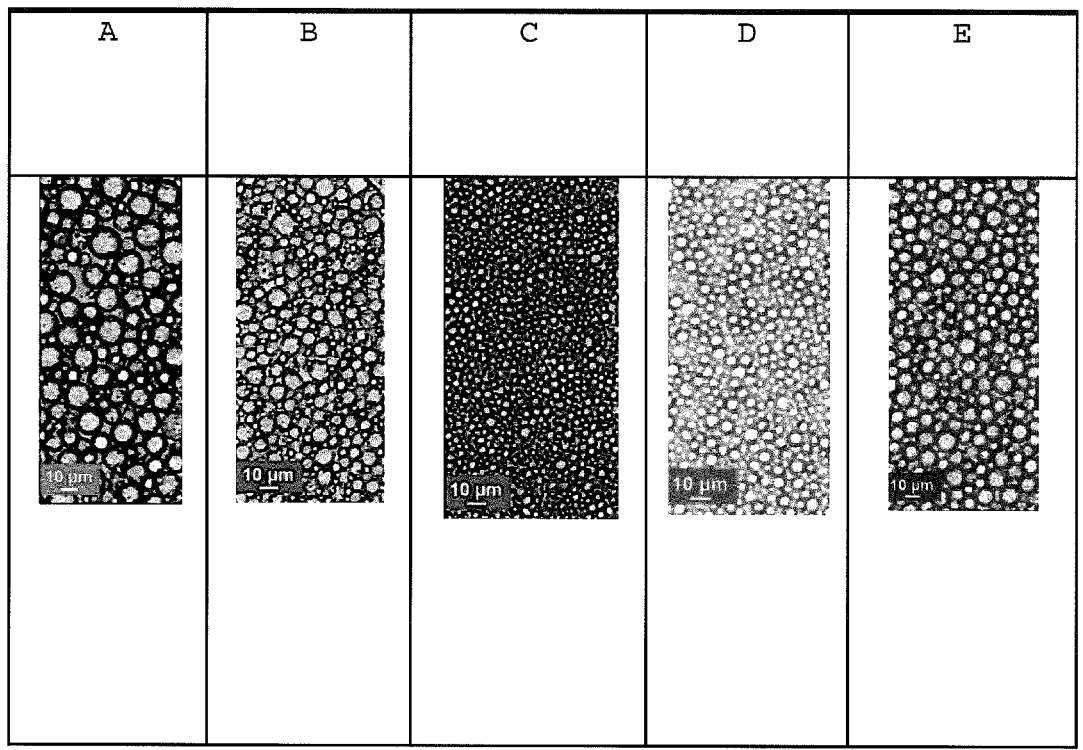
FIG. 1 shows optical microscopy views of wax dispersions comprising solid particles of beeswax having particle sizes ranging from 8-15 microns, 2-8 microns, 1-6 microns and 2-10 microns.
Figure 2:
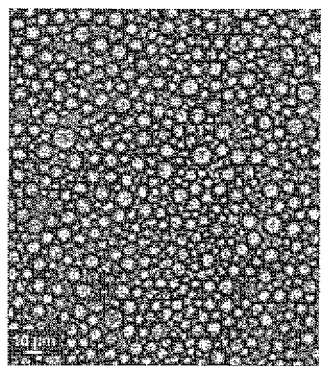
FIG. 2 shows optical microscopy view of a hair styling composition containing a wax dispersion comprising solid particles of beeswax having a particle size ranging from 4-10 microns.

As used herein, the expression "at least one" means one or more and thus includes individual components as well as mixtures/combinations.

The term "comprising" (and its grammatical variations) as used herein is used in the inclusive sense of "having" or "including" and not in the exclusive sense of "consisting only of". The terms "a" and "the" as used herein are understood to encompass the plural as well as the singular.

Other than in the operating examples, or where otherwise indicated, all numbers expressing quantities of ingredients and/or reaction conditions are to be understood as being modified in all instances by the term "about," meaning within ±10% of the indicated number.

"Film former" or "film forming agent" or "film forming agent" as used herein means a polymer or resin that leaves a film on the substrate to which it is applied, for example, after a solvent accompanying the film former has evaporated, absorbed into and/or dissipated on the substrate.

"Substituted" as used herein, means comprising at least one substituent. Non-limiting examples of substituents include atoms, such as oxygen atoms and nitrogen atoms, as well as functional groups, such as acyloxyalky groups, carboxylic acid groups, amine or amino groups, acylamino groups, amide groups, halogen containing groups, ester groups, thiol groups, sulphonate groups, thiosulphate groups, siloxane groups, and polysiloxane groups. The substituent(s) may be further substituted.

As used herein, the phrase "salts and derivatives thereof" is intended to mean all salts and derivatives comprising the same functional structure as the compound they are referring to, and that have similar properties.

As used herein, the term "applying a composition onto a substrate" and variations of this phrase are intended to mean contacting the substrate, for example, a keratinous fiber such as hair, with at least one of the compositions of the invention, in any manner.

As used herein, "formed from," means obtained from chemical reaction of, wherein "chemical reaction," includes spontaneous chemical reactions and induced chemical reactions. As used herein, the phrase "formed from," is open ended and does not limit the components of the composition to those listed.

The term "stable" as used herein means that the composition does not exhibit phase separation and/or crystallization.

The term "treat" (and its grammatical variations) as used herein refers to the application of the compositions containing the aqueous dispersion onto the surface of a substrate.

The term "shaping" (and its grammatical variations) as used herein includes styling or placing a keratinous fiber such as hair, in a particular arrangement, form or configuration; or altering the curvature of a keratinous fiber or other substrate; or re-positioning a keratinous fiber or other substrate to a different arrangement, form or configuration.

The compositions and methods of the present invention can comprise, consist of, or consist essentially of the essential elements and limitations of the invention described herein, as well as any additional or optional ingredients, components, or limitations described herein or otherwise useful.

It was surprisingly and unexpectedly discovered that the solid wax particles of the aqueous dispersion of the present disclosure can be prepared in a controlled manner by using a surfactant mixture that employs a combination of a non-ionic surfactant and an ionic surfactant and following an emulsification process. As a result, a fine dispersion of micron-sized wax particles of a narrow particle size distribution and with minimal coalescence or agglomeration can be obtained. Moreover, the solid wax particles in the aqueous dispersion of the present disclosure are advantageously substantially homogeneous with respect to their shape. Furthermore, the aqueous dispersion of the present disclosure can be formulated into compositions of various galenic forms such as gels, mousses, lotions, creams, pastes, ointments, sprays and foams. It was found that when the aqueous dispersion of the present disclosure was added into one of these galenic forms, the solid wax particles remained homogeneously and finely dispersed in the composition and said composition is stable even during storage and exhibits no agglomeration or precipitation of the solid wax particles. Moreover, the resulting composition exhibits reduced or minimized stickiness or tackiness that is generally attributed to the use of waxes.

The compositions containing the aqueous dispersion can be applied onto hair to form a film or coating.

It was also surprisingly and unexpectedly found that when the hair treated with said compositions is exposed to heat, additional benefits and attributes to the hair are achieved such as better adhesion and excellent re-shapeability and/or re-positionability.

It was also found that the treated hair may undergo further re-shaping and re-positioning when it is re-heated without the need for reapplication of the compositions containing the aqueous dispersion of the present disclosure. Said compositions also impart a clean and natural feel on the substrate, despite the presence of wax. Moreover, while the compositions containing the aqueous dispersion impart a coating or film onto hair, said compositions may easily be removed from the hair by washing with water or with conventional cleansing agents.

The attributes and benefits imparted to the hair by the application of the compositions of the present disclosure can also be observed even after the treated hair is washed. It was also surprisingly and unexpectedly found that while the compositions of the present disclosure may contain cosmetic auxiliary ingredients such as film forming agents/polymers, these agents/polymers are not required in order to obtain the benefits and attributes provided by the compositions of the present disclosure.

Although not wanting to be bound by any particular theory, it is believed that upon applying the compositions containing the aqueous dispersion onto hair in conjunction with heating the hair to a temperature around or above the melting point of the wax comprising the solid wax particle, the solid wax particles melt or soften, thereby allowing for the film or coating to be re-positioned on the hair and/or to adhere better to the hair. Thus, the solid wax particles are heat-activated or exposed to a heat stimulus in order to allow the composition containing the aqueous dispersion to achieve restylability and/or repositionability effects on the hair.

For example, heating hair with a heating device such as a flat iron or a blow dryer in conjunction with applying the hair styling compositions containing the aqueous dispersion onto hair provided re-positionability properties to the hair such that a different hair style was created without having to re-apply said compositions or without having to wash the hair first and re-applying said compositions. Thus, the use of these hair styling compositions, preferably, in combination with a heating step allows one to maintain the shape/style or to re-shape or re-position the hair, for example, straighten hair, curl hair, redefine hair curl, or volumize the hair, in an easy and convenient manner as well as in a less costly manner since one does not have to re-apply the composition.

The compositions of the present disclosure can also be used to deliver beneficial/auxiliary ingredients to the hair and to allow these ingredients to remain longer on the hair as a result of the film or coating formed on the hair.

Solid Wax Particle

The at least one solid wax particle of the aqueous dispersion has a particle size ranging from equal to or greater than 1 micron to about 100 microns, or such as from about 1 microns to about 100 microns, or such as from about 2 microns to about 100 microns, or such as from about 3 microns to about 100 microns.

Furthermore, the particle size of the at least one solid wax particle in the aqueous dispersion of the present disclosure may range from about 5 microns to about 100 microns, or from about 5 microns to about 80 microns, or such as from about 5 microns to about 50 microns, or such as from about 5 microns to about 25 microns, or such as from about 5 microns to about 12 microns, or such as from about 5 microns to about 10 microns.

The term "particle size" as used herein refers to the diameter of the particle. For non-spherical particles, the particle size refers to the largest diameter of the particles, i.e., the diameter in the dimension having the largest diameter.

Preferably, the solid wax particles in the aqueous dispersion of the present disclosure have a narrow particle size distribution, that is, the average difference in the particle sizes of the solid wax particles in an aqueous dispersion of the present disclosure is not more than about 20 microns, or not more than about 15 microns, or not more than about 10 microns, or not more than about 8 microns, or not more than about 6 microns, or not more than about 2 microns.

The shape of the solid wax particle may be spherical or ellipsoidal or oval. The terms "spherical" or ellipsoidal" or "oval" as used herein also mean that the solid wax particle has a uniform and substantially spherical or ellipsoidal or oval shape. The term "substantially" as used in the context of the shape of a spherical particle means that the particle is of substantially isotropic shape, i.e., it has a relatively regular morphology.

Thus, the ratio of the lengths of the longest to the shortest perpendicular axes of the particle cross section can be at about 1:1 or at about 1.5:1 or at about 2:1 or at about 3:1. Moreover, a line of symmetry is not required when the solid wax particle has a spherical shape. Further, the solid wax particle may have surface texturing, such as lines or indentations or protuberances that are small in scale when compared to the overall size of the solid wax particle and still be substantially spherical or ellipsoidal or oval.

The solid wax particles in the aqueous dispersion of the present disclosure are preferably substantially homogeneous with respect to their shape and particle size distribution. The term "substantially" as used in this context means that 50% of more of the solid wax particles in an aqueous dispersion of the present disclosure are of the same spherical, ellipsoidal or oval shape and of the same particle size.

The particle size and shape of the solid wax particle of the present disclosure may be evaluated by any known method such as those described in US patent application number 2006/0292095, for example, laser diffraction, ultrasonic extinction (acoustic spectroscopy), photo cross-correlation spectroscopy, granulometry, and image analysis (microscopy).

The solid wax particles of the present disclosure have a melting point greater than 35° C., such as from between greater than 35° C. to about 250° C., or such as from between greater than 35° C. to about 120° C., or such as from between about 40° C. to about 100° C.

Moreover, the solid wax particles comprise at least one wax having a melting point greater than 35° C., such as from between greater than 35° C. to about 250° C. or such as from between about 40° C. to about 100° C. The at least one wax having a melting point greater than 35° C. is defined as having a reversible change of solid/liquid state. The melting point of a wax in solid form is the same as the freezing point of its liquid form, and depends on such factors as the purity of the substance and the surrounding pressure. The melting point is the temperature at which a solid and its liquid are in equilibrium at any fixed pressure. A solid wax begins to soften at a temperature close to the melting point of the wax. With increasing temperature, the wax continues to soften/melt until at a particular temperature, the wax completely becomes liquid at a standard atmospheric pressure. It is at this stage that an actual melting point value is given for the material under consideration. When heat is removed, the liquefied wax material begins to solidify until the material is back in solid form. By bringing the wax material to the liquid state (melting), it is possible to make it miscible with other materials such as oils, and to form a microscopically homogeneous mixture. However, when the temperature of the mixture is brought to room temperature, recrystallization of the wax with the other materials in the mixture may be obtained.

The melting points of the wax(e)s and the solid wax particles of the aqueous dispersion of the present disclosure may be determined according to known methods or apparatus such as by differential scanning calorimetry, Banc Koffler device, melting point apparatus, and slip melting point measurements.

The wax(es) which comprises the at least one solid wax particle of the present disclosure and have a melting point of greater than 35° C. is chosen from waxes that are solid or semisolid at room temperature.

The wax(es) which comprises the at least one solid wax particle of the present disclosure may be chosen from waxes that have hardness values ranging from about 0.001 MPa to about 15 MPa, or such as from about 1 MPa to about 12 MPa, or such as from about 3 MPa to about 10 MPa.

The hardness of the wax may be determined by any known method or apparatus such as by needle penetration or using the durometer or texturometer.

The wax comprising the at least one solid wax particle of the present disclosure is chosen from natural and synthetic waxes.

Natural waxes include animal, vegetable/plant, mineral, or petroleum derived waxes. They are typically esters of fatty acids and long chain alcohols. Wax esters are derived from a variety of carboxylic acids and a variety of fatty alcohols. The waxes comprising the solid wax particle of the present disclosure may also be known as solid lipids.

Examples of waxes comprising the at least one solid wax particle of the present disclosure include, but are not limited to, beeswax, hydrogenated alkyl olive esters (commercially available under the trade name phytowax olive), carnauba wax, candelilla wax, ouricoury wax, Japan wax, cork fibre wax or sugar cane wax, rice wax, montan wax, paraffin wax, lignite wax or microcrystalline wax, ceresin or ozokerite, palm kernel glycerides/hydrogenated palm glycerides and hydrogenated oils such as hydrogenated castor oil or jojoba oil, sugarcane, retamo, bayberry, rice bran, soy, castor, esparto, japan waxes, hydroxyoctacosanyl hydroxystearate, Chinese wax, cetyl palmitate, lanolin, shellac, and spermaceti; synthetic waxes such as those of the hydrocarbon type and polyethylene waxes obtained from the polymerization or copolymerization of ethylene, and Fischer-Tropsch® waxes, or else esters of fatty acids, such as octacosanyl stearate, glycerides which are solid at temperatures of above 35° C., silicone waxes, such as alkyl- or alkoxydimethicones having an alkyl or alkoxy chain ranging from 10 to 45 carbon atoms, poly(di)methylsiloxane esters which are solid at 30° C. and whose ester chain comprising at least 10 carbon atoms, or else di(1,1,1-trimethylolpropane) tetrastearate, which is sold or manufactured by Heterene under the name HEST® 2T-4S, and mixtures thereof.

Other examples of waxes or solid lipids include C20-40 di- and triglycerides, including those which contain unsaturated fatty acids, C20-40 fatty alcohols, C2-40 fatty amines and their compounds, and sterols.

The table below lists waxes whose melting points are greater than 35° C. and which are suitable for use in accordance with the present disclosure:

| INCI name and/or Trade name | Melting point (mp) |
| --- | --- |
| Paraffin wax | 57.3° C. |
| Stearic alcohol | 58.8° C. |
| Carnauba wax | 82.3° C. |
| Ozokerite | 66.8° C. |
| microcrystalline wax | 83.3° C. |
| polyethylene wax | 95.6° C. * |
| Hydrogenated Castor oil | 85.07° C. |
| synthetic beeswax | 51.2° C. * |
| wax AC 540 | 98.4° C. * |
| Beeswax | 62.6° C. |
| Candelilla wax | 64.3° C. |
| Hydroxyoctacosanyl Hydroxystearate | 76.8° C. |
| Hydrogenated Castor wax | 81.7° C. |
| wax AC 400 | 86.3° C. |
| PVP/Eicosene Copolymer | 37.8° C. |
| polyethylene wax | 83.9° C. |
| Hydrogenated Jojoba wax | 69.4° C. |
| palm butter | 58.4° C. |
| rice bran wax | 78.6° C. * |
| sumac wax | 48.3° C. |
| polyglycerol beeswax | 63.1° C. |
| Tricontanyl/PVP | 68.8° C. * |
| C20-40 Alkyl Stearate | 72.5° C. |
| siliconyl beeswax | 53.4° C. |
| Stearyl Stearate | 57.1° C. |
| polyethylene wax | 71.8° C. |
| polyethylene wax | 92.9° C. |
| ceresin wax | 60.1° C. |
| Ultrabee WD | 61.3° C. |
| Phytowax Olive 14 L 48 (hydrogenated myristyl olive esters) | 46.02° C. |
| Phytowax Olive 18 L 57 (hydrogenated stearyl olive esters) | 58.6° C. |
| Alcohol polyethylene wax | 95.7° C. |
| Koster wax K82P (anc.K80P) | 69.6° C. |
| *Citrus Aurantium Dulcis* (Orange) Peel Wax | 40.7° C. |
| Pentaerythritol Distearate | 48.5° C. |
| *Theobroma Grandiflorum* Seed Butter | 36.94° C. |
| DI 18/22 ADIPATE | 64.13° C. |
| DI 18/22 SEBACATE | 66.44° C. |
| DI 18/22 OCTANEDIOATE | 75.15° C. |
| *Helianthus Annuus* (Sunflower) Seed Wax | 75.46° C. |

-continued

| INCI name and/or Trade name | Melting point (mp) |
|---|---|
| K82P-S | 67.97° C. |
| K82P-VS | 66.20° C. |
| Silicone resin wax (Dow Corning ® SW-8005) | 54.3-65.6° C. |
| Polymethylalkyl dimethylsiloxane | 67.8° C. * |
| Alcohol polyethylene wax | 76.2° C. |
| Pentaerythrityl tetrastearate | 63.0° C. |
| Tetracontanyl Stearate | 65.1° C. |
| fatty acid wax | 63.7° C. |
| Fischer-tropsch wax | 79.3° C. * |
| behenyl alcohol | 66.9° C. |
| alkyl dimethicone wax | 57.0° C. |
| Stearyl Benzoate | 40.6° C. |
| Berry wax | 47.5° C. |
| Chinese insect wax | 81.1° C. * |
| Shellac wax | 73.8° C. * |
| Behenyl fumarate | 74.5° C. |
| Koster BK-42 | 40.5° C. * |
| Koster KPC-56 | 58.5° C. |
| Koster KPC-60 | 61.7° C. |
| Koster KPC-63 | 65.2° C. |
| Koster KPC-80 | 55.6° C. |
| siliconyl candellila wax | 66.8° C. |
| Koster BK-37 | 38.0° C. |
| Ditrimethylolpropane tetrastearate | 46.5° C. |
| Synthetic Wax | 70.7° C. |
| Clariant Licowax KST 1 | 55.2° C. |
| Betawax RX-13750 | 72.0° C. |
| Dipentaerythrytol hexastearate | 67.7° C. |
| Ditrimethylolpropane tetrabehenate | 67.5° C. |
| Behenyl methacrylate grafted PDMS | 48.6° C. |
| Jojoba esters | 56.7° C. |
| Waxolive | 55.8° C. |
| Inholive | 40.3° C. |
| Phytowax Ricin 16 L 64 | 69.1° C. * |
| Phytowax Ricin 22 L 73 | 76.6° C. |
| Burco LB-02 | 45.1° C. |
| Hydrogenated Castor Oil Isostearate | 52.5° C. |
| Hydrogenated Castor Oil Isostearate | 54.0° C. * |
| Vegetable Wax | 81.0° C. |
| Hydrogenated *Macadamia* Seed Oil | 51.49° C. |
| Synthetic Wax | 51.4° C. |
| Dioctadecyl Carbonate | 56.7° C. |
| Montan Wax | 63.4° C. |
| *Citrus Medica Limonum* (Lemon) Peel Extract | 58.3° C. |

* with several melting point peaks

Particularly preferred waxes having a melting point of greater than 35° C. are beeswax, commercially available from various suppliers, hydrogenated stearyl olive ester, and commercially available from the supplier Sophim under the tradename, Phytowax Olive 18 L 57, hydrogenated myristyl olive ester, and commercially available from the supplier Sophim under the tradename, Phytowax Olive 14 L 48, VP/eicosene copolymer, commercially available from the supplier ISP under the tradenames, Antaron® V 220 or Ganex® V 220F, and ditrimethyloylpropane tetrastearate, commercially available from the supplier Heterene under the tradename, HEST 2T-4S.

Other particularly preferred waxes having a melting point of greater than 35° C. are silicone waxes, including silsesquioxane resin waxes such as C30-45 alkyldimethylsilyl propylsilsesquioxane, commercially available as DOW CORNING SW-8005 C30 Resin Wax, from the company Dow Corning and such as those described in WO2005/100444.

The wax(es) which comprises the at least one solid wax particle of the present disclosure have a melting point of greater than 35° C., or may range from about 40° C. to about 100° C., or such as from about 40° C. to about 80° C. The wax(es) which comprises the at least one solid wax particle of the present disclosure may be chosen from soft waxes and from hard waxes. Soft waxes may be defined as those waxes which have a melting point of below about 70° C., and preferably, a melting point of below about 60° C. Hard waxes may be defined as those waxes which have a melting point of equal to or greater than about 70° C., and preferably, a melting point of equal to or greater than about 60° C.

According to one embodiment, soft waxes according to the present disclosure include, but are not limited to, Paraffin wax, stearic alcohol, ozokerite, synthetic beeswax, beeswax, candelilla wax, PVP/eicosene copolymer, hydrogenated jojoba wax, palm butter, sumac wax, polyglyceryl beeswax, tricontanyl/PVP, siliconyl beeswax, stearyl stearate, ceresin wax, hydrogenated myristyl olive esters (e.g., phytowax olive 14 L 48), hydrogenated stearyl olive esters (e.g., phytowax olive 18 L 57), Koster K82P, orange peel wax, Pentaerythritol distearate, *Theobroma Grandiflorum* Seed Butter, silicone resin wax, Polymethylalkyl dimethylsiloxane, Pentaerythrityl tetrastearate, Tetracontanyl Stearate, fatty acid wax, behenyl alcohol, alkyl dimethicone wax, Stearyl Benzoate, Berry wax, koster wax, siliconyl candelilla wax, Ditrimethylolpropane tetrastearate, Clariant Licowax KST 1, Dipentaerythrytol hexastearate, Ditrimethylolpropane tetrabehenate, Behenyl methacrylate gréffé PDMS, jojoba esters, waxolive, inholive, phytowax ricin 16 L 64, hydrogenated macadamia seed oil, synthetic wax, dooctadecyl carbonate, montan wax, lemon peel extract, ditrimethyloylpropane tetrastearate, and C30-45 alkyldimethylsilyl propylsilsesquioxane. (check melting points of last two)

According to one embodiment, hard waxes according to the present disclosure, include, but are not limited to, carnauba wax, microcrystalline wax, polyethylene wax, hydrogenated castor oil, wax AC 540, Hydroxyoctacosanyl Hydroxystearate, hydrogenated castor wax, wax AC 400, rice bran wax, C20-40 alkyl stearate, Alcohol polyethylene wax, octanedioate, sunflower seed wax, fischer-tropsch wax, Chinese insect wax, shellac wax, benehyl fumarate, synthetic wax, betsawax RX-13750, phytowax ricin 22 L 73, and vegetable wax.

The wax having a melting point of greater than 35° C. and comprising the at least one solid wax particle of the present disclosure may be employed in an amount ranging from about 10% to about 80% by weight, or preferably from about 15% to about 60% by weight, or preferably from about 20% to about 40% by weight, based on the total weight of the aqueous dispersion of the present disclosure, including all ranges and subranges therebetween.

In certain embodiments, the aqueous dispersions of the present disclosure comprise solid wax particles having different properties with respect to hardness and/or melting point and/or shape and/or size.

The wax having a melting point of greater than 35° C. and comprising the at least one solid wax particle of the present disclosure may be employed in an amount ranging from about 0.5% to about 20% by weight, or preferably from about 1% to about 10% by weight, or more preferably from about 2% to about 8% by weight, or even more preferably from about 2% to about 5% by weight, based on the total weight of the composition of the present disclosure, including all ranges and subranges therebetween.

Additional Ingredients

The solid wax particle can further comprise additional ingredients such as waxes having melting points of 35° C. or less, oils, emulsifying polymers, silicas, talc, clays, ceramides, and perfumes. These additional ingredients can be added during the time of making the aqueous dispersion in order to either improve/modify the physical properties of the solid wax particles and/or to allow the solid wax particles to provide other benefits in addition to the benefits obtained from waxes.

Waxes Having Melting Points of 35° C. or Less

Suitable additional waxes that may further comprise the solid wax particle are those waxes whose melting points are at 35° C. or less; these waxes include, but are not limited to, Hest 2T-5E-45, Ditrimethylolpropane tetralaurate, Koster BK-34, Fluoro Polymethylalkyl dimethylsiloxane, Blend of Dilauryl Adipate and Ditetradecyl Adipate, Astrocaryum MuruMuru Seed Butter, *Myrica Pubescens* Wax, PEG-70 Mango Glycerides, oxypropylenated lanolin wax, hydrogenated Coco-glycerides.

Nevertheless, the waxes whose melting points are at 35° C. or less are selected such that the resulting melting point of the solid wax particle of the present disclosure is greater than 35° C.

Oils

Suitable oils that may comprise the solid wax particle include, but are not limited to, mineral oils (paraffin); plant oils and natural oils (sweet almond oil, macadamia oil, grapeseed oil, olive oil, argan oil, tocopherol or vitamin E, shea butter oil, jojoba oil); synthetic oils, for instance perhydrosqualene, fatty acids or fatty esters (for instance the $C_{12}$-$C_{15}$ alkyl benzoate sold under the trade name Finsolv® TN, commercially available from Innospec or Tegosoft® TN, commercially available from Evonik Goldschmidt, octyl palmitate, isopropyl lanolate and triglycerides, including capric/caprylic acid triglycerides), oxyethylenated or oxypropylenated fatty esters and ethers; or fluoro oils, and polyalkylenes.

Other oils include for example: silicone oils, for instance volatile or non-volatile polymethylsiloxanes (PDMS) with a linear or cyclic silicone chain, which are liquid or pasty at room temperature, especially cyclopolydimethylsiloxanes (cyclomethicones) such as cyclohexasiloxane; polydimethyl-siloxanes comprising alkyl, alkoxy or phenyl groups, which are pendent or at the end of a silicone chain, these groups containing from 2 to 24 carbon atoms; phenyl silicones, for instance phenyl trimethicones, phenyl dimethicones, phenyltrimethylsiloxydiphenyl-siloxanes, diphenyl dimethicones, diphenylmethyl-diphenyltrisiloxanes or 2-phenylethyl trimethylsiloxy silicates, and polymethylphenylsiloxanes; mixtures thereof.

Other suitable oils include, but are not limited to, volatile hydrocarbon-based oils such as, for example, volatile hydrocarbon oils having from 8 to 16 carbon atoms and their mixtures and in particular branched $C_8$ to $C_{16}$ alkanes such as $C_8$ to $C_{16}$ isoalkanes (also known as isoparaffins), isododecane, isodecane, isohexadecane, and for example, the oils sold under the trade names of Isopar™ or Permethyl®, and their mixtures.

Other suitable oils include esters such as those of formula $R_1COOR_2$ in which $R_1$ represents a linear or branched higher fatty acid residue containing from 1 to 40 carbon atoms, including from 7 to 19 carbon atoms, and $R_2$ represents a branched hydrocarbon-based chain containing from 1 to 40 carbon atoms, including from 3 to 20 carbon atoms, and also including, for example, octyldodecyl neopentanoate, Purcellin oil (cetostearyl octanoate), isononyl isononanoate, $C_{12}$ to $C_{15}$ alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate, and pentaerythritol esters. Other suitable esters include polyesters, alkoxylated esters, and alkoxylated polyesters.

The oils may also be chosen from silicones. Suitable silicones include, but are not limited to, the silicone oils described above and other silicones such as non-volatile silicones such as dimethicone fluids having viscosity values of equal to or greater than 300 cst, and pentaphenyldimethicone, also known as trimethyl pentaphenyl trisiloxane, commercially available from Dow Corning under the tradename Dow Corning® 555.

The oil(s) that may further comprise the solid wax particle of the present disclosure is selected such that the melting point of the solid wax particle is greater than 35° C. Preferably, the ratio of oil to wax(es) ranges from between 1:100 to 20:100.

Emulsifying Polymers

The solid wax particles of the aqueous dispersion of the present disclosure may also comprise an emulsifying polymer, i.e. an amphiphilic polymer.

Among the emulsifying polymers that are suitable for use in the invention, mention may be made of:

POE-POP diblock and triblock copolymers such as those described in U.S. Pat. No. 6,464,990;

polyoxyethylenated silicone surfactants such as those described in U.S. Pat. No. 6,120,778;

non-crosslinked hydrophobic AMPSs such as those described in EP 1 466 588;

amphiphilic acrylic polymers, such as PEMULEN TR-1 or TR-2 or equivalent;

the associative and gelling polymers described in US 2003/0138465;

heat-gelling polymers such as those described in patent applications US 2004/0214913, US 2003/0147832 and US 2002/0198328 and FR2 856 923.

When they are present, the emulsifying polymer(s) may be introduced in a content ranging from 0.1 percent to 15 percent by weight, or even from 0.1 percent to 10 percent by weight and more particularly from 0.1 percent to 5 percent by weight relative to the total weight of the aqueous dispersion.

Sunscreen Agents

The solid wax particle may further comprise one or more sunscreen agents. Representative sunscreen agents may be chosen from organic and inorganic sunscreens or UV filters.

The organic sunscreen agents are selected from water-soluble organic screening agents, fat-soluble organic screening agents or agents which are insoluble in the solvents presently included in suntan products, and mixtures thereof.

The organic sunscreen agents are especially selected from cinnamic derivatives; anthranilates; salicylic derivatives; dibenzoylmethane derivatives; camphor derivatives; benzophenone derivatives; beta, beta-diphenylacrylate derivatives; triazine derivatives; benzotriazole derivatives; benzalmalonate derivatives; benzimidazole derivatives; imidazolines; bis-benzazolyl derivatives; p-aminobenzoic acid (PABA) derivatives; methylenebis(hydroxyphenylbenzotriazole) derivatives; benzoxazole derivatives; screening polymers and screening silicones; alpha-alkylstyrene-derived dimers; 4,4-diarylbutadienes; merocyanin derivatives; and mixtures thereof.

Examples of complementary organic photoprotective agents include those denoted hereinbelow under their INCI name:

Cinnamic Derivatives: Ethylhexyl Methoxycinnamate marketed in particular under the trademark "Parsol MCX®" by DSM Nutritional Products, Inc., Isopropyl Methoxycinnamate, Isoamyl p-Methoxycinnamate marketed under the trademark "Neo Heliopan E 1000®" by Symrise, DEA Methoxycinnamate, Diisopropyl Methylcinnamate, Glyceryl Ethylhexanoate Dimethoxycinnamate.

Dibenzoylmethane Derivatives: [Butyl Methoxydibenzoylmethane marketed especially under the trademark "Parsol 1789®" by DSM Nutritional Products, Inc., Isopropyl Dibenzoylmethane.

Para-Aminobenzoic Acid Derivatives: PABA, Ethyl PABA, Ethyl Dihydroxypropyl PABA, Ethylhexyl Dimethyl PABA marketed in particular under the trademark "Escalol 507®" by ISP, Glyceryl PABA, PEG-25 PABA marketed under the trademark "Uvinul P25®" by BASF.

Salicylic Derivatives: Homosalate marketed under the trademark "Eusolex HMS®" by Merck KGaA/EMD Chemicals, Inc. and EMD Chemicals Inc, Ethylhexyl Salicylate marketed under the trademark "Neo Heliopan OS®" by Symrise, Dipropylene Glycol Salicylate marketed under the trademark "Dipsal™" by Lubrizol Advanced Materials, Inc., TEA Salicylate marketed under the trademark "Neo Heliopan® TS" by Symrise.

Diphenylacrylate Derivatives: Octocrylene marketed in particular under the trademark "Uvinul N539T®" by BASF, Etocrylene marketed in particular under the trademark "Uvinul® N35" by BASF.

Benzophenone Derivatives: Benzophenone-1 marketed under the trademark "Uvinul® 400" by BASF, Benzophenone-2 marketed under the trademark "Uvinul® D50" by BASF, Benzophenone-3 or Oxybenzone marketed under the trademark "Uvinul® M40" by BASF, Benzophenone-4 marketed under the trademark "Uvinul® MS40" by BASF, Benzophenone-5, Benzophenone-6 marketed under the trademark "Helisorb® 11" by Norquay, Benzophenone-8, Benzophenone-9, Benzophenone-12, n-Hexyl 2-(4-diethylamino-2-hydroxybenzoyl)benzoate marketed under the trademark "Uvinul® A+" by BASF.

Benzylidenecamphor Derivatives: 3-Benzylidenecamphor manufactured under the trademark "Mexoryl™ SD" by Chimex, 4-Methylbenzylidenecamphor marketed under the trademark "Eusolex® 6300" by Merck, Benzylidene Camphor Sulfonic acid manufactured under the trademark "Mexoryl™ SL" by Chimex, Camphor Benzalkonium Methosulfate manufactured under the trademark "Mexoryl™ SO" by Chimex, Terephthalylidene Dicamphor Sulfonic acid manufactured under the trademark "Mexoryl™ SX" by Chimex, Polyacrylamidomethyl Benzylidene Camphor manufactured under the trademark "Mexoryl™ SW" by Chimex.

Phenylbenzimidazole Derivatives: Phenylbenzimidazole Sulfonic acid marketed in particular under the trademark "Eusolex® 232" by Merck and EMD INC., Disodium Phenyl Dibenzimidazole Tetrasulfonate marketed under the trademark "Neo Heliopan® AP" by Symrise.

Phenylbenzotriazole Derivatives: Drometrizole Trisiloxane, Methylene bis(Benzotriazolyl) Tetramethylbutylphenol, or in micronized form as an aqueous dispersion under the trademark "Tinosorb® M" by BASF.

Triazine Derivatives: bis-Ethylhexyloxyphenol Methoxyphenyl Triazine marketed under the trademark "Tinosorb® S" by BASF, Ethylhexyl Triazone marketed in particular under the trademark "Uvinul® T150" by BASF, Diethylhexyl Butamido Triazone marketed under the trademark "Uvasorb® HEB" by 3V Group, 2,4,6-Tris(dineopentyl 4'-aminobenzalmalonate)-s-triazine, 2,4,6-Tris(diisobutyl 4'-aminobenzalmalonate)-s-triazine, 2,4-Bis(n-butyl 4'-aminobenzoate)-6-(aminopropyltrisiloxane)-s-triazine, 2,4-Bis(dineopentyl 4'-aminobenzalmalonate)-6-(n-butyl 4'-amino benzoate)-s-triazine, triazine agents, especially 2,4,6-tris(biphenyl-1,3,5-triazines (in particular 2,4,6-tris(biphenyl-4-yl)-1,3,5-triazine and 2,4,6-tris(terphenyl)-1,3,5-triazine.

Anthranilic Derivatives: Menthyl anthranilate marketed under the trademark "Neo Heliopan® MA" by Symrise.

Imidazoline Derivatives: Ethylhexyl Dimethoxybenzylidene Dioxoimidazoline Propionate.

Benzalmalonate Derivatives: Polyorganosiloxane containing benzalmalonate functions, for instance Polysilicone-15, marketed under the trademark "Parsol® SLX" by DSM Nutritional Products, Inc.

4,4-Diarylbutadiene Derivatives: 1,1-Dicarboxy(2,2'-dimethylpropyl)-4,4-diphenylbutadiene.

Benzoxazole derivatives: 2,4-Bis[5-(1-dimethylpropyl) benzoxazol-2-yl(4-phenyl)imino]-6-(2-et-hylhexyl)imino-1,3,5-triazine marketed under the trademark Uvasorb K 2A by Sigma 3V, and mixtures thereof.

The preferred organic sunscreen agents are selected from: Ethylhexyl Methoxycinnamate, Ethylhexyl Salicylate, Homosalate, Butyl Methoxydibenzoylmethane, Octocrylene, Phenylbenzimidazole Sulfonic Acid, Benzophenone-3, Benzophenone-4, Benzophenone-5, n-Hexyl 2-(4-diethylamino-2-hydroxybenzoyl)benzoate, 4-Methylbenzylidene camphor, Terephthalylidene Dicamphor Sulfonic Acid, Disodium Phenyl Dibenzimidazole Tetrasulfonate, Methylene bis-Benzotriazolyl Tetramethylbutylphenol, Bis-Ethylhexyloxyphenol Methoxyphenyl Triazine, Ethylhexyl Triazone, Diethylhexyl Butamido Triazone, 2,4,6-Tris (dineopentyl 4'-aminobenzalmalonate)-s-triazine, 2,4,6-Tris (diisobutyl 4'-aminobenzalmalonate)-s-triazine, 2,4-Bis(n-butyl 4'-aminobenzoate)-6-(aminopropyltrisiloxane)-s-triazine, 2,4-Bis(dineopentyl 4'-aminobenzalmalonate)-6-(n-butyl 4'-aminobenzoate)-s-triazine, 2,4,6-Tris(biphenyl-4-yl)-1,3,5-triazine, 2,4,6-Tris(terphenyl)-1,3,5-triazine, Drometrizole Trisiloxane, Polysilicone-15, 1,1-Dicarboxy (2,2'-dimethylpropyl)-4,4-diphenylbutadiene, 2,4-Bis[5-1-(dimethylpropyl)benzoxazol-2-yl(4-phenyl)imino]-6-(2-et-hylhexyl)-imino-1,3,5-triazine, and mixtures thereof.

Examples of inorganic sunscreen agents or UV filters include, but are not limited to, metal oxide pigments which may be chosen from zinc oxide, titanium oxide, iron oxide, zirconium oxide, cerium oxide, and mixtures thereof.

The metal oxide pigments may be coated or uncoated.

The coated pigments are pigments that have undergone one or more surface treatments of chemical, electronic, mechanochemical and/or mechanical nature with compounds such as amino acids, beeswax, fatty acids, fatty alcohols, anionic surfactants, lecithins, sodium potassium, zinc, iron or aluminum salts of fatty acids, metal alkoxides (of titanium or of aluminum), polyethylene, silicones, proteins (collagen, elastin), alkanolamines, silicon oxides, metal oxides or sodium hexametaphosphate.

Preferably, the sunscreen agents that may be comprise the solid wax particle are oil-soluble (or fat-soluble) and may be encapsulated within low melting point temperature materials.

The sunscreen agents of the present invention may be employed in an amount of from about 0.1% to about 40% by weight, such as from about 0.5% to about 30% by weight, such as from about 1% to about 25% by weight, based on the total weight of the solid wax particle comprising the aqueous dispersion.

Pigments/Dyes

The pigments/dyes that may further comprise the solid wax particle are preferably soluble in oil and include, but are not limited to, permanent, semi-permanent and/or temporary dyes.

Representative pigments include white, colored, inorganic, organic, polymeric, nonpolymeric, coated and uncoated pigments. Representative examples of mineral pigments include titanium dioxide, optionally surface-treated, zirconium oxide, zinc oxide, cerium oxide, iron oxides, chromium oxides, manganese violet, ultramarine blue, chromium hydrate, and ferric blue. Representative examples of organic pigments include carbon black, pigments of D & C type, and lakes based on cochineal carmine, barium.

The direct dyes and oxidation dyes which may be used in the present invention are those dyes employed to color hair and textile fabrics. Representative oxidation dyes include, but are not limited to para-phenylenediamines, bis(phenyl) alkylenediamines, para-aminophenols, ortho-aminophenols and heterocyclic bases, and the addition salts thereof. Representative direct dyes include, but are not limited to, azo, methane, carbonyl, azine, nitro (hetero)aryl, tri(hetero)arylmethane, porphyrin, phthalocyanin direct dyes, and natural direct dyes.

Silicas, Talc, and Clays

The solid wax particle may further comprise sub-micron-sized to micron-sized particles of silica, talc, and/or clays, which include, but are not limited to, montmorillonite, bentonite, hectorite, attapulgite, sepiolite, laponite, smectite, kaolin, and their mixtures.

These clays can be modified with a chemical compound chosen from quaternary ammoniums, tertiary amines, amine acetates, imidazo lines, amine soaps, fatty sulphates, alkylarylsulphonates, amine oxides and their mixtures.

Mention may be made, as organophilic clays, of quaternium-18 bentonites, such as those sold under the names Bentone 3, Bentone 38 or Bentone 38V by Rheox, Tixogel VP by United Catalyst or Claytone 34, Claytone 40 or Claytone XL by Southern Clay; stearalkonium bentonites, such as those sold under the names Bentone 27 by Rheox, Tixogel LG by United Catalyst or Claytone AF or Claytone APA by Southern Clay; or quaternium-1 8/benzalkonium bentonites, such as those so ld under the names Claytone HT or Claytone PS by Southern Clay.

Suitable silicas may include pyrogenic silicas obtained by high temperature hydrolysis of a volatile silicon compound in an oxyhydrogen flame, producing a finely divided silica. This process makes it possible in particular to obtain hydrophilic silicas which exhibit a large number of silanol groups at their surfaces.

It is possible to chemically modify the surface of the silica by a chemical reaction for the purpose of decreasing the number of silanol groups. It is possible in particular to substitute silanol groups by hydrophobic groups: a hydrophobic silica is then obtained.

The hydrophobic groups can be:
trimethylsiloxyl groups, which are obtained in particular by treatment of pyrogenic silica in the presence of hexamethyldisilazane. Silicas thus treated are also named "Silica silylate."
dimethylsilyloxyl or polydimethylsiloxane groups, which are obtained in particular by treatment of pyrogenic silica in the presence of polydimethylsiloxane or of dimethyldichlorosilane. Silicas thus treated are also named "Silica dimethyl silylate."

The pyrogenic silica preferably exhibits a particle size which can be sub-micron sized or micron sized, for example ranging from approximately 5 to 200 nm.

The silica, talc, and/or clays may be present in an amount of from about 0.01% to about 10% by weight, or preferably, from about 0.5% to about 2% by weight, based on the weight of the aqueous dispersion.

Ceramides

Ceramide compounds that may be useful according to various embodiments of the disclosure include ceramides, glycoceramides, pseudoceramides, and mixtures thereof. The ceramides which may be chosen include, but are not limited to, those described by DOWNING in Arch. Dermatol, Vol. 123, 1381-1384 (1987), DOWNING in Journal of Lipid Research, Vol. 35, page 2060 (1994), or those described in French patent FR 2673179.

Further exemplary ceramides that may be used according to various embodiments of the disclosure include, but are not limited to, compounds of the general formula (I):

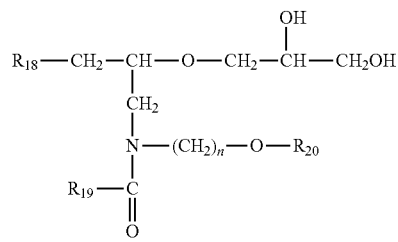

wherein, in formula (I):
$R_{18}$ and $R_{19}$ are, independently, chosen from alkyl- or alkenyl groups with 10 to 22 carbon atoms,
$R_{20}$ is chosen from methyl, ethyl, n-propyl or isopropyl groups, and
n is a number ranging from 1 to 6, such as, for example, 2 or 3.

In further embodiments, ceramide compounds may be chosen from compounds of formula (II), as described in US20050191251 and US20090282623:

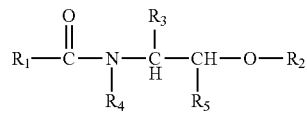

wherein, in formula (II):
$R_1$ is chosen from either a saturated or unsaturated, linear or branched $C_1$-$C_{50}$, e.g. $C_5$-$C_{50}$, hydrocarbon radical, it being possible for this radical to be substituted with one or more hydroxyl groups optionally esterified with an acid $R_7COOH$, $R_7$ being an optionally mono- or polyhydroxylated, linear or branched, saturated or unsaturated $C_1$-$C_{35}$ hydrocarbon radical, it being possible for the hydroxyl(s) of the radical $R_7$ to be esterified with an optionally mono- or polyhydroxylated, linear or branched, saturated or unsaturated $C_2$-$C_{35}$ fatty acid, or a radical R"—(NR—CO)—R', R being chosen from a hydrogen atom or a mono- or polyhydroxylated, e.g. monohydroxylated, $C_1$-$C_{20}$ hydrocarbon radical, R' and R" chosen from, independently, hydrocarbon radicals of which the sum of the carbon atoms is between 9 and 30, R' being a divalent radical, or a radical $R_8$—O—CO—$(CH_2)p$, $R_8$ denoting a $C_1$-$C_{20}$ hydrocarbon radical, p being an integer varying from 1 to 12;

$R_2$ being chosen from a hydrogen atom, a saccharide-type radical, in particular a (glycosyl)n, (galactosyl)m and sulphogalactosyl radical, a sulphate or phosphate residue, a phosphorylethylamine radical and a phosphorylethylammonium radical, in which n is an integer varying from 1 to 4 and m is an integer varying from 1 to 8;

$R_3$ chosen from a hydrogen atom or a hydroxylated or nonhydroxylated, saturated or unsaturated, $C_1$-$C_{33}$ hydrocarbon radical, it being possible for the hydroxyl(s) to be esterified with an inorganic acid or an acid $R_7$COOH, $R_7$ having the same meanings as above, and it being possible for the hydroxyl(s) to be etherified with a (glycosyl)n, (galactosyl)m, sulphogalactosyl, phosphorylethylamine or phosphorylethylammonium radical, it being also possible for $R_3$ to be substituted with one or more $C_1$-$C_{14}$ alkyl radicals;

$R_4$ being chosen from a hydrogen atom, a methyl or ethyl radical, an optionally hydroxylated, linear or branched, saturated or unsaturated $C_3$-$C_{50}$ hydrocarbon radical or a radical —$CH_2$—CHOH—$CH_2$—O—$R_6$ in which $R_6$ denotes a $C_{10}$-$C_{26}$ hydrocarbon radical or a radical $R_8$—O—CO—$(CH_2)p$, $R_8$ chosen from a $C_1$-$C_{20}$ hydrocarbon radical, p being an integer varying from 1 to 12; and $R_5$ denotes a hydrogen atom or an optionally mono- or polyhydroxylated, linear or branched, saturated or unsaturated $C_1$-$C_{30}$ hydrocarbon radical, it being possible for the hydroxyl(s) to be etherified with a (glycosyl)n, (galactosyl)m, sulphogalactosyl, phosphorylethylamine or phosphorylethylammonium radical, with the proviso that when $R_3$ and $R_5$ denote hydrogen or when $R_3$ denotes hydrogen and $R_5$ denotes methyl, then $R_4$ does not denote a hydrogen atom, or a methyl or ethyl radical.

By way of example, ceramides of formula (IV) may be chosen from those wherein $R_1$ is an optionally hydroxylated, saturated or unsaturated alkyl radical derived from $C_{14}$-$C_{22}$ fatty acids; $R_2$ is a hydrogen atom; and $R_3$ is an optionally hydroxylated, saturated, linear $C_{11}$-$C_{17}$, e.g. $C_{13}$-$C_{15}$ radical.

In yet further embodiments, ceramide compounds useful according to the disclosure may be chosen from compounds of the general formula (III):

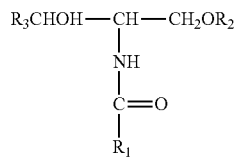

wherein, in formula (III):

$R_1$ is chosen from a linear or branched, saturated or unsaturated alkyl group, derived from $C_{24}$-$C_{30}$ fatty acids, it being possible for this group to be substituted with a hydroxyl group in the alpha-position, or a hydroxyl group in the omega-position esterified with a saturated or unsaturated $C_{26}$-$C_{30}$ fatty acid;

$R_2$ is chosen from a hydrogen atom or a (glycosyl)$_n$, (galactosyl)$_m$ or sulphogalactosyl group, in which n is an integer ranging from 1 to 4 and m is an integer ranging from 1 to 8; and $R_3$ is chosen from a $C_5$-$C_{26}$ hydrocarbon-based group, saturated or unsaturated in the alpha-position, it being possible for this group to be substituted with one or more $C_1$-$C_{14}$ alkyl groups; it being understood that, in the case of natural ceramides or glycoceramides, $R_3$ may also be chosen from a $C_5$-$C_{26}$ alpha-hydroxyalkyl group, the hydroxyl group being optionally esterified with a $C_{16}$-$C_{30}$ alpha-hydroxy acid.

Exemplary ceramides of formula (III) which may be chosen include compounds wherein $R_1$ is chosen from a saturated or unsaturated alkyl derived from $C_6$-$C_{22}$ fatty acids; $R_2$ is chosen from a hydrogen atom; and $R_3$ is chosen from a linear, saturated $C_{15}$ group. By way of non-limiting example, such compounds may be chosen from N-linoleoyl-dihydrosphingosine, N-oleoyldihydrosphingosine, N-palmitoyldihydro-sphingosine, N-stearoyldihydrosphingosine, N-behenoyldihydrosphingosine, or mixtures thereof.

As further non-limiting examples of ceramides, compounds wherein $R_1$ is chosen from a saturated or unsaturated alkyl group derived from fatty acids; $R_2$ is chosen from a galactosyl or sulphogalactosyl group; and $R_3$ is chosen from the group —CH=CH—$(CH_2)_{12}$—$CH_3$ group, may be used. In at least one exemplary embodiment, the product consisting of a mixture of these compounds, sold under the trade name Glycocer, by the company Waitaki International Biosciences, may be used.

As further exemplary ceramides, mention may be made of the following ceramides, as described in US20110182839.

In further embodiments, ceramide compounds useful according to the disclosure may be chosen from compounds of the general formula (IV):

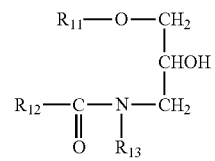

wherein, in formula (IV):

$R_{11}$ and $R_{12}$ are, independently, chosen from alkyl or alkenyl groups with 10 to 22 carbon atoms, $R_{13}$ is an alkyl or hydroxyl alkyl group with 1 to 4 carbon atoms, and n is a number ranging from 1 to 6, such as, for example, 2 or 3.

In at least one embodiment, the at least one ceramide compound is chosen from cetyl-PG-hydroxyethylpalmitamide. In a further embodiment, the at least one ceramide compound is chosen from propanediamide, N,N-dihexadecyl-N,N-bis-(2-hydroxyethyl), such as that sold commercially as Questamide H or Pseudoceramide H by the company Quest International Australia Pty. Ltd. In yet a further embodiment, the at least one ceramide compound is chosen from Cetyl-PG Hydroxylpalmatide/decyl glucoside/water, sold as SOFCARE P100H by Kao.

The at least one ceramide compound is present in an amount ranging from 0.001 percent to 20 percent by weight, for example, from 0.01 percent to 10 percent by weight and further for example, from 0.1 percent to 0.5 percent by weight, relative to the total weight of the composition. In one embodiment, the at least one ceramide compound may be present in an amount of 0.5 percent by weight, relative to the total weight of the aqueous dispersion.

Perfumes

The solid wax particle may further comprise perfumes or fragrances to aid in the fragrance of the product and provide a time-release effect. The perfume can have a dual effect by not only providing a pleasant fragrance but also to provide shine to a treated substrate. The perfumes may be present in an amount of from about 0.01% to about 10% by weight, or preferably, from about 0.5% to about 2% by weight, based on the weight of the aqueous dispersion.

Surfactant Mixture

The surfactant mixture of the present disclosure comprises at least one non ionic surfactant and at least one ionic surfactant.

In general, nonionic surfactants having a Hydrophilic-Lipophilic Balance (HLB) of from at least 5, such as from about 5 to about 20, or such as from about 5 to about 15, are contemplated for use by the present invention. Nonlimiting examples of nonionic surfactants useful in the compositions of the present invention are disclosed in McCutcheon's "Detergents and Emulsifiers," North American Edition (1986), published by Allured Publishing Corporation; and McCutcheon's "Functional Materials," North American Edition (1992); both of which are incorporated by reference herein in their entirety.

Examples of nonionic surfactants useful herein include, but are not limited to, alkoxylated derivatives of the following: fatty alcohols, alkyl phenols, fatty acids, fatty acid esters and fatty acid amides, wherein the alkyl chain is in the $C_{12}$-$C_{50}$ range, preferably in the $C_{16}$-$C_{40}$ range, more preferably in the $C_{24}$ to $C_{40}$ range, and having from about 1 to about 110 alkoxy groups. The alkoxy groups are selected from the group consisting of $C_2$-$C_6$ oxides and their mixtures, with ethylene oxide, propylene oxide, and their mixtures being the preferred alkoxides. The alkyl chain may be linear, branched, saturated, or unsaturated. Of these alkoxylated non-ionic surfactants, the alkoxylated alcohols are preferred, and the ethoxylated alcohols and propoxylated alcohols are more preferred. The alkoxylated alcohols may be used alone or in mixtures thereof. The alkoxylated alcohols may also be used in mixtures with those alkoxylated materials disclosed herein-above.

Other representative examples of such ethoxylated fatty alcohols include laureth-3 (a lauryl ethoxylate having an average degree of ethoxylation of 3), laureth-23 (a lauryl ethoxylate having an average degree of ethoxylation of 23), ceteth-10 (a cetyl alcohol ethoxylate having an average degree of ethoxylation of 10) steareth-10 (a stearyl alcohol ethoxylate having an average degree of ethoxylation of 10), and steareth-2 (a stearyl alcohol ethoxylate having an average degree of ethoxylation of 2), steareth-100 (a stearyl alcohol ethoxylate having an average degree of ethoxylation of 100), beheneth-5 (a behenyl alcohol ethoxylate having an average degree of ethoxylation of 5), beheneth-10 (a behenyl alcohol ethoxylate having an average degree of ethoxylation of 10), and other derivatives and mixtures of the preceding.

Also available commercially are Brij® nonionic surfactants from Uniqema, Wilmington, Del. Typically, Brij® is the condensation products of aliphatic alcohols with from about 1 to about 54 moles of ethylene oxide, the alkyl chain of the alcohol being typically a linear chain and having from about 8 to about 22 carbon atoms, for example, Brij® 72 (i.e., Steareth-2) and Brij® 76 (i.e., Steareth-10).

Also useful herein as nonionic surfactants are alkyl glycosides, which are the condensation products of long chain alcohols, e.g. $C_8$-$C_{30}$ alcohols, with sugar or starch polymers. These compounds can be represented by the formula (S)n-O—R wherein S is a sugar moiety such as glucose, fructose, mannose, galactose, and the like; n is an integer of from about 1 to about 1000, and R is a $C_8$-$C_{30}$ alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants are alkyl polyglucosides wherein S is a glucose moiety, R is a $C_8$-$C_{20}$ alkyl group, and n is an integer of from about 1 to about 9. Commercially available examples of these surfactants include decyl polyglucoside (available as APG® 325 CS) and lauryl polyglucoside (available as APG® 600CS and 625 CS), all the above-identified polyglucosides APG® are available from Cognis, Ambler, Pa. Also useful herein are sucrose ester surfactants such as sucrose cocoate and sucrose laurate.

Other nonionic surfactants suitable for use in the present invention are glyceryl esters and polyglyceryl esters and their derivatives, including but not limited to, glyceryl monoesters, preferably glyceryl monoesters of $C_{16}$-$C_{22}$ saturated, unsaturated and branched chain fatty acids such as glyceryl oleate, glyceryl monostearate, glyceryl monoisostearate, glyceryl monopalmitate, glyceryl monobehenate, and mixtures thereof, and polyglyceryl esters of $C_{16}$-$C_{22}$ saturated, unsaturated and branched chain fatty acids, such as polyglyceryl-4 isostearate, polyglyceryl-3 oleate, polyglyceryl-2 sesquioleate, triglyceryl diisostearate, diglyceryl monooleate, tetraglyceryl monooleate, and mixtures thereof. glyceryl ester derivatives include, but are not limited to, polyethylene glycol ethers of glyceryl esters such as PEG-30 glyceryl stearate, PEG-30 glyceryl diisostearate, PEG-30 glyceryl isostearate, PEG-30 glyceryl laurate, PEG-30 glyceryl oleate, and mixtures thereof.

Also useful herein as nonionic surfactants are sorbitan esters. Preferable are sorbitan esters of $C_{16}$-$C_{22}$ saturated, unsaturated and branched chain fatty acids. Because of the manner in which they are typically manufactured, these sorbitan esters usually comprise mixtures of mono-, di-, tri-, etc. esters. Representative examples of suitable sorbitan esters include sorbitan monooleate (e.g., SPAN® 80), sorbitan sesquioleate (e.g., Arlacel® 83 from Uniqema, Wilmington, Del.), sorbitan monoisostearate (e.g., CRILL® 6 from Croda, Inc., Edison, N.J.), sorbitan stearates (e.g., SPAN® 60), sorbitan trioleate (e.g., SPAN® 85), sorbitan tristearate (e.g., SPAN® 65), sorbitan palmitate (e.g., SPAN® 40), and sorbitan isostearate. Sorbitan palimtate and sorbitan sesquioleate are particularly preferred for use in the present disclosure.

Also suitable for use herein are alkoxylated derivatives of glyceryl esters, sorbitan esters, and alkyl polyglycosides, wherein the alkoxy groups is selected from the group consisting of $C_2$-$C_6$ oxides and their mixtures, with ethoxylated or propoxylated derivatives of these materials being the preferred. Nonlimiting examples of commercially available ethoxylated materials include TWEEN® (ethoxylated sorbitan mono-, di- and/or tri-esters of $C_{12}$ to $C_{18}$ fatty acids with an average degree of ethoxylation of from about 2 to about 20).

Preferred nonionic surfactants are those formed from a fatty alcohol, a fatty acid, or a glyceride with a $C_4$ to $C_{36}$ carbon chain, preferably a $C_{12}$ to $C_{18}$ carbon chain, more preferably a $C_{16}$ to $C_{18}$ carbon chain, derivatized to yield an HLB of at least 8. HLB is understood to mean the balance between the size and strength of the hydrophilic group and the size and strength of the lipophilic group of the surfactant. Such derivatives can be polymers such as ethoxylates, propoxylates, polyglucosides, polyglycerins, polylactates, polyglycolates, polysorbates, and others that would be apparent to one of ordinary skill in the art. Such derivatives may also be mixed polymers of the above, such as ethoxylate/propoxylate species, where the total HLB is preferably greater than or equal to 8. Preferably the nonionic surfactants contain ethoxylate in a molar content of from 10-25, more preferably from 10-20 moles.

Particularly preferred nonionic surfactants of the present disclosure are chosen from polyethylene glycol ethers of glyceryl esters, PEG-30 glyceryl stearate and sorbitan esters such as sorbitan palmitate.

The nonionic surfactant will typically be employed in an amount of from about 60% to about 95% by weight, or from about 65% to about 90% by weight, or from about 70% to about 90% by weight, based on the total weight of the surfactant mixture of the present disclosure.

Typically, the ionic surfactants contain a lipophilic hydrocarbon group and a polar functional hydrophilic group.

The following anionic surfactants, which may be used alone or as mixtures, may be mentioned: mention may be made especially of the salts, in particular the alkali metal salts such as the sodium salts, the ammonium salts, the amine salts, the amino alcohol salts or the salts of alkaline-earth metals, for example of magnesium, of the following compounds: alkyl sulfates, alkyl ether sulfates, alkylamido ether sulfates, alkylaryl polyether sulfates, monoglyceride sulfates; alkylsulfonates, alkyl phosphates, alkylamidesulfonates, alkylarylsulfonates, a-olefin sulfonates, paraffin sulfonates; alkyl sulfosuccinates, alkyl ether sulfosuccinates, alkylamide sulfosuccinates; alkyl sulfoacetates; acylsarcosinates; and acylglutamates, the alkyl or acyl groups of all these compounds comprising from 6 to 24 carbon atoms and the aryl group preferably denoting a phenyl or benzyl group. It is also possible to use esters of C6-C24 alkyl and of polyglycoside-carboxylic acids, such as alkyl glucoside citrates, polyalkyl glycoside tartrates and polyalkyl glycoside sulfosuccinates; alkyl sulfosuccinamates, acyl isethionates and N-acyltaurates, the alkyl or acyl group of all these compounds containing from 12 to 20 carbon atoms. Among the anionic surfactants that may also be used, mention may also be made of acyl lactylates in which the acyl group contains from 8 to 20 carbon atoms. Mention may also be made of alkyl-D-galactosideuronic acids and salts thereof, and also polyoxyalkylenated (C6-C24)alkylether-carboxylic acids, polyoxyalkylenated (C6-C24)alkyl(C6-C24)aryleth-ercarboxylic acids and polyoxyalkylenated (C6-C24)alky-lamidoethercarboxylic acids and salts thereof, in particular those comprising from 2 to 50 ethylene oxide groups, and mixtures thereof.

Among the preferred anionic surfactants, mention may be made of the salts, in particular of sodium, of magnesium or of ammonium, of alkyl sulfates; of alkyl ether sulfates, for instance sodium lauryl ether sulfate, preferably containing 2 or 3 mol of ethylene oxide; of acyl glutamates, for instance, disodium stearoyl glutamate and sodium stearoyl glutamate; of alkyl ether carboxylates; and mixtures thereof, the alkyl or acyl groups generally containing from 6 to 24 carbon atoms and preferably from 8 to 16 carbon atoms.

Among the cationic surfactants, mention may be made of:

i) alkylpyridinium salts, ammonium salts of imidazoline, diquaternary ammonium salts, and ammonium salts containing at least one ester function;

ii) quaternary ammonium salts having the following general formula:

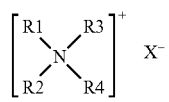

(I)

in which the radicals R1 to R4, which may be identical or different, represent a linear or branched aliphatic radical containing from 1 to 30 carbon atoms, or an aromatic radical such as aryl or alkylaryl; the aliphatic radicals may optionally comprise heteroatoms (O, N, S or halogens) and may optionally, be substituted.

The aliphatic radicals are chosen, for example, from C12-C22 alkyl, alkoxy, C2-C6 polyoxyalkylene, alkylamide, (C12-C22)alkylamido(C2-C6)alkyl, (C12-C22)alkyl-acetate and hydroxyalkyl radicals, containing from 1 to 30 carbon atoms. X— is an anion chosen from the group of halides, phosphates, acetates, lactates, C2-C6 alkyl sulfates and alkyl or alkylarylsulfonates.

iii) quaternary ammonium salts of imidazoline of formula:

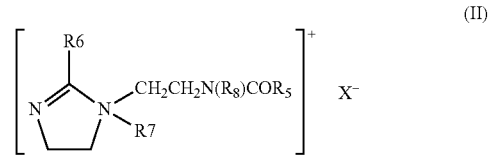

(II)

in which:

R5 represents an alkenyl or alkyl radical containing from 8 to 30 carbon atoms, for example fatty acid derivatives of tallow or of coconut, R6 represents a hydrogen atom, a C1-C4 alkyl radical or an alkenyl or alkyl radical containing from 8 to 30 carbon atoms, R7 represents a C1-C4 alkyl radical, R8 represents a hydrogen atom or a C1-C4 alkyl radical, X' is an anion chosen from the group of halides, phosphates, acetates, lactates, C2-C6 alkyl sulfates, alkylsulfonates or alkylarylsulfonates.

R5 and R6 preferably denote a mixture of alkenyl or alkyl radicals containing from 12 to 21 carbon atoms, such as, for example, fatty acid derivatives of tallow, R7 denotes methyl and R8 denotes hydrogen. Such a product is, for example, Quaternium-27 (CTFA 1997) or Quaternium-83 (CTFA 1997), which are sold under the names Rewoquat® W75, W90, W75PG and W75HPG by the company Witco, iv) diquaternary ammonium salts of formula:

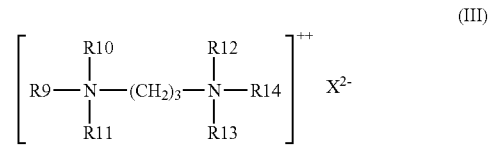

(III)

in which:

R9 denotes an aliphatic radical containing from about 16 to 30 carbon atoms,

R10, R11, R12, R13 and R14, which may be identical or different, are chosen from hydrogen and an alkyl radical containing from 1 to 4 carbon atoms, and X— is an anion chosen from the group of halides, acetates, phosphates, nitrates, ethyl sulfates and methyl sulfates.

Such diquaternary ammonium salts in particular comprise propanetallowdiammonium dichloride;

v) quaternary ammonium salts containing at least one ester function, such as those of formula:

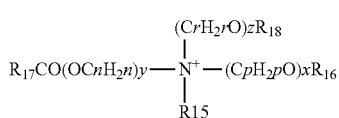 (IV)

in which:

R15 is chosen from C1-C6 alkyl radicals and C1-C6 hydroxyalkyl or dihydroxyalkyl radicals;

R16 is chosen from the radical R19-CO—, linear or branched, saturated or unsaturated C1-C22 hydrocarbon-based radicals R20, a hydrogen atom;

R18 is chosen from the radical R21-CO, linear or branched, saturated or unsaturated C1-C22 hydrocarbon-based radicals R22, a hydrogen atom;

R17, R19 and R21, which may be identical or different, are chosen from linear or branched, saturated or unsaturated C7-C21 hydrocarbon-based radicals;

r, n and p, which may be identical or different, are integers ranging from 2 to 6;

y is an integer ranging from 1 to 10;

x and z, which may be identical or different, are integers ranging from 0 to 10;

X— is a simple or complex organic or mineral anion;

with the proviso that the sum x+y+z is from 1 to 15, that when x is 0, then R16 denotes R20 and that when z is 0, then R18 denotes R22.

The alkyl radicals R15 may be linear or branched, and more particularly linear. Preferably, R15 denotes a methyl, ethyl, hydroxyethyl or dihydroxypropyl radical, and more particularly a methyl or ethyl radical.

Advantageously, the sum x+y+z is from 1 to 10.

When R16 is a hydrocarbon-based radical R20, it may contain from 12 to 22 carbon atoms, or contain from 1 to 3 carbon atoms.

When R18 is a hydrocarbon-based radical R22, it preferably contains 1 to 3 carbon atoms.

Advantageously, R17, R19 and R21, which may be identical or different, are chosen from linear or branched, saturated or unsaturated C11-C21 hydrocarbon-based radicals, and more particularly from linear or branched, saturated or unsaturated C11-C21 alkyl and alkenyl radicals.

Preferably, x and z, which may be identical or different, are equal to 0 or 1. Advantageously, y is equal to 1.

Preferably, r, n and p, which may be identical or different, are equal to 2 or 3 and even more particularly equal to 2.

The anion X— is preferably a halide (chloride, bromide or iodide) or a C1-C4 alkyl sulfate, more particularly methyl sulfate. The anion X— may also represent methanesulfonate, phosphate, nitrate, tosylate, an anion derived from an organic acid (such as acetate or lactate), or any other anion that is compatible with the ammonium containing an ester function.

The surfactants may be, for example, the salts (chloride or methyl sulfate) of diacyloxyethyldimethylammonium, of diacyloxyethylhydroxyethyldimethylammonium, of monoacyloxyethylhydroxyethyldimethylammonium, of triacyloxyethylmethylammonium, of monoacyloxyethylhydroxyethyldimethylammonium, and mixtures thereof. The acyl radicals preferably contain 14 to 18 carbon atoms and are more particularly derived from a plant oil, for instance palm oil or sunflower oil. When the compound contains several acyl radicals, these radicals may be identical or different.

Such compounds are sold, for example, under the names Dehyquart® by the company Cognis, Stepanquat® by the company Stepan, Noxamium® by the company Ceca, and Rewoquat® WE 18 by the company Rewo-Goldschmidt.

vi) quaternary ammonium salts and in particular behenyltrimethylammonium chloride, dipalmitoylethylhydroxyethylmethylammonium methosulfate, cetyltrimethylammonium chloride, quaternium-83, behenylamidopropyl-2,3-dihydroxypropyldimethylammonium chloride and palmitylamidopropyltrimethylammonium chloride.

Other suitable cationic surfactants are esterquats which are quaternary ammonium compounds having fatty acid chains containing ester linkages.

Among the preferred cationic surfactants, mention may be made of compounds of formula (I) chosen from cetrimonium chloride, behentrimonium chloride, Behenyl PG-Trimonium chloride, dicetyl dimonium chloride, and mixtures, thereof.

Other preferred cationic surfactant are esterquats chosen from Dibehenoylethyl Dimonium Chloride, Dipalmitoylethyl Dimonium Chloride, Distearoylethyl Dimonium Chloride, Ditallowoyl PG-dimonium Chloride, Dipalmitoylethyl hydroxyethylmonium methosulfate, Distearoylethyl hydroxyethylmonium methosulfate, and mixtures, thereof.

Without being bound by any one theory, it is believed that the presence of an ionic surfactant, particularly, at the time of making the dispersion, reduces or minimizes the aggregation of the solid wax particles in the aqueous dispersion of the present disclosure. Thus, the surfactant mixture comprising at least one ionic surfactant acts as a dispersant to facilitate the uniform dispersion of the solid wax particles and to enhance the stabilization of the dispersion itself.

In certain embodiments of the present disclosure, the surfactant mixture contains at least one nonionic surfactant and at least one ionic surfactant comprising at least one anionic surfactant.

In other embodiments, the surfactant mixture contains at least one nonionic surfactant and at least one ionic surfactant comprising at least one cationic surfactant.

In preferred embodiments, the surfactant mixture contains at least one nonionic surfactant and at least one ionic surfactant comprising at least one anionic surfactant wherein the surfactant mixture is free of cationic surfactants.

In yet other preferred embodiments, the surfactant mixture contains at least one nonionic surfactant and at least one ionic surfactant comprising at least one cationic surfactant wherein the surfactant mixture is free of anionic surfactants.

The at least one ionic surfactant will typically be employed in an amount of from about 5% to about 40% by weight, or from about 5% to 30% by weight, or from about 5% to about 20% by weight, based on the total weight of the surfactant mixture of the present disclosure.

Preferably, the surfactant mixture, that is, the combined amount of the at least one nonionic surfactant and the at least one ionic surfactant is present in the aqueous dispersion in an amount of from about 1.0% to about 5% by weight, or such as from about 1.5% to about 3.5% by weight, or such as from about 1.5% to about 3% by weight, based on the total weight of the aqueous dispersion.

In certain preferred embodiments, the surfactant mixture of the present disclosure is free of amphoteric surfactants.

Amphoteric surfactants include, but are not limited to, aliphatic secondary or tertiary amine derivatives, in which the aliphatic group is a linear or branched chain containing 8 to 22 carbon atoms and containing at least one water-soluble anionic group, such as, for example, a carboxylate, sulfonate, sulfate, phosphate or phosphonate group; mention may also be made of (C8-C20)alkylbetaines, sulfobetaines, (C8-C20)alkyl-amido-(C6-C8)-alkyl-betaines or (C8-C20) alkyl-amido-(C6-C8)-alkylsulfobetaines; and mixtures thereof.

Among the amine derivatives that may be mentioned are amphocarboxyglycinate compounds and amphocarboxypropionate compounds, in particular, disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid and cocoamphodipropionic acid, (C8-C20)alkylbetaines, (C8-C20)alkylamido(C6-C8)alkylbetaines and alkylamphodiacetates.

Among the amphoteric surfactants that may be preferably used are (C8-C20)alkylbetaines, (C8-C20)alkylamido(C6-C8)alkylbetaines and alkylamphodiacetates, and mixtures thereof.

Process for Obtaining the Aqueous Dispersions (Wax Dispersion Protocol)

The aqueous dispersions of the present disclosure may be obtained by means of a process comprising at least the steps as follow:

emulsifying a mixture containing at least one wax having a melting point or melting temperature greater than 35° C., a surfactant mixture comprising a nonionic surfactant and an ionic surfactant, and water at an emulsification temperature above the melting point of the at least one wax. If two or more waxes are used, the emulsification temperature should be higher than the melting point of the wax with the higher or highest melting point, subjecting the mixture to a process leading to the production of solid wax particles, at a temperature at least 5 to 10° C. above the emulsification temperature of the mixture used in the preceding step, and cooling the dispersion thus obtained.

It is pointed out that the combination of ingredients in the first step of the process and the execution of the second step with heating are cumulative conditions necessary for obtaining the solid wax particles according to the invention in a controlled manner, resulting in solid wax particles that are calibrated to certain properties (e.g., melting point, size, and shape). Thus, the nature of the process exerted on the wax-surfactant-water mixture determines the properties of the particles to be obtained.

The process according to the invention may, where appropriate, also include a step consisting in diluting the continuous phase of the mixture before the cooling step.

For the purposes of the present invention, the expression "process leading to the production of solid wax particles" is intended to denote an action of shear type. This shearing action can be accomplished by mixing the wax-surfactant-water mixture using a homogenizer/mixer at a specified speed.

For example, by using different speeds of mixing, different particle sizes can be achieved such as those ranging from 0.5-100 microns, 1-50 microns, 2-25 microns, 8-20 microns, 2-10 microns, and even less than 1 micron. It is also possible to use other shearing processes such as those described and referred to in US2006/0292095 and US2006/0263438.

The amounts and the types of surfactants in and/or the weight ratios of the surfactants to one another the surfactant mixture and/or the amounts and/or types of waxes employed may also result in wax particles of different particle sizes such as those listed above.

The emulsification temperature is preferably greater than 40 degrees C. and preferably less than 95 degrees C.

Thus, in accordance with the process above, the dispersions of the present disclosure comprise solid wax particles that are calibrated to specific properties. Moreover, these particles are preferably free of volatile solvent.

Furthermore, in accordance with the process above, other ingredients, such as active ingredients, polymers, and other additional ingredients as described above may be added during the preparation of the dispersion.

Dispersion

In accordance with the process described above, the solid wax part particles are preferably obtained as a dispersion in a aqueous and/or water-soluble continuous phase. Such a dispersion may also be described as an oil-in-water emulsion or an oil-in-water dispersion.

The solid wax particles in accordance with the invention advantageously do not aggregate in the dispersion in which they are obtained, and their granulometric specificities in terms of size and distribution index are advantageously conserved therein.

The aqueous and/or water-soluble continuous phase that is suitable for use in the invention preferably comprises water or a combination of water and a water-soluble organic solvent.

Among the water-soluble solvents that may be used in the dispersions in accordance with the invention, mention may be made especially of lower monoalcohols containing from 1 to 5 carbon atoms, such as ethanol and isopropanol, glycols, glycol ethers, and polyols, for instance glycerol, ethylene glycol, propylene glycol, butylene glycol, caprylyl glycol, hexylene glycol, dipropylene glycol, diethylene glycol, xylitol, sorbitol, mannitol, maltitol, and polyethylene glycol or mixtures thereof, C3 and C4 ketones, and C2-C4 aldehydes and mixtures thereof.

For the purposes of the present invention, the term "water-soluble solvent" is intended to denote a compound that is liquid at room temperature and water-miscible (miscibility in water of greater than 50 percent by weight at 25° C. and at atmospheric pressure).

According to yet another embodiment variant, the dispersions in accordance with the present invention may comprise demineralized water as the continuous aqueous phase.

The aqueous dispersions of the present disclosure are formulated into hair styling compositions of various galenic forms.

The hair styling compositions containing the aqueous dispersions of the present disclosure include a cosmetically acceptable carrier chosen from water, volatile and non-volatile organic solvents, silicones, polyols, glycols, glycol ethers, oils, and mixtures thereof.

When the organic solvent is a volatile solvent, the amount of the volatile organic solvent generally ranges from greater than 0 (e.g., about 0.01%) to about 99%, and in some embodiments from greater than 0 to about 55%, and in some embodiments from greater than 0 to about 2%, by weight, based on the total weight of the composition. In certain embodiments, the amount of volatile organic solvent does not exceed 55%.

The cosmetically acceptable carrier is non toxic and may also be dermatologically or physiologically acceptable.

The cosmetically acceptable carrier can be employed in an amount of from about 70% to about 99% by weight, or such as from about 75% to about 95% by weight, or such as from about 80% to about 90% by weight, based on the total weight of the composition.

Auxiliary Agent

The compositions comprising the aqueous dispersion of the present disclosure may additionally contain an auxiliary agent chosen from liquid lipids/oils, film forming polymers, rheology modifiers, sunscreen agents, pigments, dyes, silica, clays, humectants and moisturizing agents, emulsifying agents, structuring agents, propellants, surfactants, shine agents, conditioning agents, cosmetically, dermatologically and pharmaceutically active agents, vitamins, and plant extracts.

Liquid Lipids/Oils

Representative liquid lipids comprise oils, triglycerides and liquid fatty substances such as mineral oil, avocado oil, camellia oil, turtle oil, macadamia nut oil, corn oil, mink oil, olive oil, rape seed oil, egg yolk oil, sesame oil, persic oil, wheat germ oil, sasanqua oil, castor oil, linseed oil, safflower oil, cottonseed oil, perilla oil, soybean oil, peanut oil, tea seed oil, kaya oil, rice bran oil, chinese-wood oil, japanese-wood oil, jojoba oil, germ oil, triglycerol, glyceryl trioctanoate, pentaerythritol tetraoctanote, and glyceryl triisopalmitate.

Film Forming Polymers

The term "film forming polymer" means a polymer capable, by itself or in the presence of an auxiliary film-forming agent, of forming a continuous film that adheres to a support and especially to keratin materials. Among the film-forming polymers that may be used, mention may be made of synthetic polymers, of free-radical type or of polycondensate type, polymers of natural origin and mixtures thereof, in particular acrylic polymers, polyurethanes, polyesters, polyamides, polyureas and cellulose-based polymers, for instance nitrocellulose.

Rheology Modifiers

Representative rheology modifiers include, but are not limited to, thickening agents, and gelling agents.

Broadly, the rheology modifier(s) that may be useful in the practice of the present invention include those conventionally used in cosmetics such as polymers of natural origin and synthetic polymers, including, but not limited to, associative polymers, non-associative thickening polymers, and water-soluble thickening polymers.

Representative rheology-modifiers that may be used in the practice of the present invention may be chosen from nonionic, anionic, cationic, and amphoteric polymers, including acrylate- or acrylic-based polymers, polysaccharides, polyamino compounds, and nonionic, anionic, cationic and amphoteric amphiphilic polymers.

Suitable rheology modifiers include but are not limited to, acrylates copolymers and carbomers. Other suitable rheology modifiers include, but are not limited to, cellulose-based thickeners (e.g., hydroxyethylcellulose, hydroxypropylcellulose, carboxymethylcellulose, cationic cellulose ether derivatives, quaternized cellulose derivatives, etc.), guar gum and its derivatives (e.g., hydroxypropyl guar, cationic guar derivatives, etc.), gums such as gums of microbial origin (e.g., xanthan gum, scleroglucan gum, etc.), and gums derived from plant exudates (e.g., gum arabic, ghatti gum, karaya gum, gum tragacanth, carrageenan gum, agar gum and carob gum), pectins, alginates, and starches, crosslinked homopolymers of acrylic acid or of acrylamidopropanesulfonic acid.

The rheology modifiers of the present disclosure may also be used as film forming agents in the compositions and aqueous dispersions of the present disclosure, depending on the amount employed.

Examples of rheology modifiers of the present disclosure are polyacrylate-3, commercially known under the trade name of Viscophobe DB-100 and commercially available from The Dow Chemical Company, carbomers, commercially known under the trade name of Carbopol polymers and commercially available from Lubrizol Advance Materials, Inc, acrylates/C10-30 alkyl acrylate crosspolymers, commercially known the trade names of Pemulen TR-1 and Pemulen TR-2 polymers and commercially available from Lubrizol Advance Materials, Inc, AMP-acrylates/allyl methacrylate copolymer, commercially known under the trade name of Fixate G-100 polymer and commercially available from Lubrizol Advance Materials, Inc and polyvinylpyrrolidone, commercially known under the trade name of PVP and commercially available from International Specialty Products.

The rheology modifier is typically present in an amount ranging from about 0.01% to about 10% by weight, in some embodiments from about 0.1% to about 5% by weight, based on the total weight of the composition.

Sunscreen Agents, Pigments, Dyes, Silica and Clays

Representative sunscreen agents which comprise the solid wax particle as described above may also comprise the compositions of the present disclosure.

The pigments and dyes, silicas and clays described above which may comprise the solid wax particle of the aqueous dispersion may also comprise the compositions of the present disclosure.

Humectants and Moisturizing Agents

Suitable examples of humectants and moisturizing agents include, but are not limited to urea, hydroxyethyl urea, polyols such as glycerin, and glycosaminoglycans (GAGS). Suitable examples of glycosaminoglycans are hyaluronic acid or hyaluronan (HA), heparan sulfate (HS), heparin (HP), chondroitin, chondroitin sulfate (CS), chondroitin 4-sulfate or chondroitin sulfate A (CSA), chondroitin 6-sulfate or chondroitin sulfate C (CSC), dermatan sulfate or chondroitin sulfate B (CSB) and keratan sulfate (KS).

Propellants

Representative examples of propellants include n-butane, isobutane, propane, dimethyl ether (available commercially from Harp Int'l under the tradename HARP DME), C2-C5 halogenated hydrocarbons, e.g., 1,1-difluoroethane (available commercially from DuPont under the tradename DYMEL 152a), difluoroethane, chlorodifluoroethane, dichlorodifluoromethane, chlorodifluoromethane, trichlorofluoromethane, and mixtures thereof. The amount of the propellant generally ranges from about 1 to about 55%, and in some embodiments from about 1 to about 35%, by weight, and in some embodiments from about 1 to about 20%, by weight and in some embodiments from about 2 to about 15%, by weight based on the total weight of the composition.

Surfactants

The surfactants that may be employed as auxiliary agents may be chosen from anionic, cationic, nonionic and amphoteric surfactants such as those described above.

Shine Agents

The shine agents may be chosen from silicones, alkoxylated silicones, oils, ethoxylated oils, fats, esters, transesters, hydrocarbons, quats and mixtures thereof.

Non-limiting examples of shine agents include Amodimethicone, Dimethicone, Dimethiconol, Cyclemethicone, Phenyltrimethicone, Aminopropyl Phenyltrimethicone, Trimethyl Pentaphenyl Trisiloxane, Cetyl Dimethicone, Alkyl Dimethicone, Potassium Dimethicone PEG-7 Pantheyl Phosphate, Olive oil, Jojoba oil, Apricot oil, Avocado oil, Castor oil, Lanolin, Squalane, Capric/Caprylic Triglyceride, Octyl Palmitate, Isopropyl Palmitate, Isopropyl Myristate, Mineral oil, Petrolatum, Polyquaternium-4, Polyquaternium-11, Behentrimonium Methosulfate, Benetrimonium Chloride and mixtures thereof.

The aqueous dispersions of the present disclosure may additionally comprise one or more additives chosen from pearlescent agents, opacifying agents, fragrances, sequestering agents, softeners, antifoams, wetting agents, spreading agents, dispersants, plasticizers, mineral fillers, colloidal minerals, peptizers, preserving agents, and pH adjusters.

The compositions comprising the aqueous dispersions of the present disclosure may be in the form of an aqueous system, a simple or complex emulsion (oil-in-water (o/w), water-in-oil (w/o), silicone-in-water and/or water-in-silicone emulsion types) such as a cream or a milk, in the form of a gel or a cream-gel, or in the form of a lotion, a powder or a solid tube, and may optionally be packaged as an aerosol and may be in the form of a mousse or a spray. The mousse or spray may contain propellants such as those listed above.

Spray compositions, especially aerosols, typically contain at least one volatile organic compound (VOC). For essentially ecological reasons and governmental regulations in various countries, it is sought or even necessary to reduce the amount of volatile organic compounds (VOCs) present in the composition. To reduce the amount of VOC and to obtain a low-VOC aerosol device, the organic solvents, for instance ethanol and dimethyl ether, are partially replaced with water.

When the compositions of the present disclosure are emulsions, they will generally contain at least one emulsifier/surfactant chosen from amphoteric, anionic, cationic and nonionic emulsifiers or surfactants, which are used alone or as a mixture. The emulsifiers are appropriately chosen according to the emulsion to be obtained.

In another embodiment of the invention, the subject compositions are formulated as water-in-silicone (W/Si) or silicone-in-water (Si/W) emulsions in which the continuous oily phase comprises at least one silicone oil. When the compositions of the invention are formulated as water-in-silicone emulsions, the silicone oils are preferably present in a proportion of at least 5 percent and preferably ranging from 10 percent to 45 percent by weight with respect to the total weight of the emulsion. The fatty phase of the water-in-oil emulsions according to the invention can additionally comprise one or more hydrocarbon-comprising oil(s) in a proportion preferably ranging up to 40 percent by weight with respect to the total weight of the fatty phase of the emulsion.

For the W/Si emulsions, examples of emulsifiers generally include polyether-modified silicones having a long chain of dimethyl siloxane units which carry polyethoxy-polypropoxy units in the chain and at the ends. Examples include cyclopentasiloxane PEG/PPG-18/18 dimethicone, PEG-12 Dimethicone, and PEG/PPG-19/19 Dimethicone sold by Dow Corning under the name Dow Corning® BY 11-030.

The hair styling compositions of the present disclosure are applied onto hair in order to impart a shape or re-positionability or re-shapeability properties to the hair.

In preferred embodiments, the application of an external stimulus such as heat onto the hair may be desirable or required in order to allow the hair styling composition to impart additional benefits to the hair. Thus, the solid wax particles comprising the aqueous dispersion are heat-activated wherein the application of heat to the hair allows the solid wax particle in the composition to melt. In order to melt the solid wax particle, the heat applied to the hair has to be at a temperature greater than the melting point of the solid wax particles or of the wax that has the highest melting point, if two or more waxes comprise the solid wax particle.

Thus, in some embodiments, a method of shaping hair is provided, wherein said method involves applying onto the hair, a composition containing the aqueous dispersion of the present disclosure, and a cosmetically acceptable carrier and heating the hair in order to melt the solid wax particles in the aqueous dispersion. The hair may then be shaped or positioned to achieve a certain style or appearance.

Professional and consumer heating tools can be used as a means to deliver heat or an elevated temperature to the hair. The heating tools can generate heat through electrical current or heating lamps. Depending upon the desired style, these tools include, but are not limited to, heaters, blow dryers, flat irons, hot combs, hot curler sets, steam pods, heated crimpers, heated lash curlers, heated wands/brushes, and hood driers or their combinations thereof The above-described method allows one to shape/re-shape or re-position the hair on the head, such as to straighten the hair, curl the hair, redefine hair curl, or volumize the hair, and to repeat the steps of said method as many times as desired and without needing to re-apply the composition and/or re-wet the hair.

In particularly preferred embodiments, a means for shaping the hair is used. The means for physically shaping the hair may be part of the heating tool or may be a separate device or tool such as a brush or comb or curling device. The means for physically shaping the hair may also comprise passing the fingers or the hand through the hair.

The steps of the above-described method for shaping hair may be conducted in any order. For example, the composition containing the aqueous dispersion may first be applied onto hair, followed by heating the hair, then followed by shaping the hair using a means for shaping the hair. In another example, the hair may be heated first, followed by the step of applying the composition onto the hair, then followed by the step of shaping the hair using a means for shaping the hair. In yet another example, the hair may be shaped first, using a means for shaping the hair, followed by applying the composition onto the hair and then heating the hair. In other examples, the hair may be shaped first using a means for shaping the hair, followed by heating the hair and then applying the composition onto the hair and allowing the shape of the hair to set in place as the temperature reaches room temperature.

The compositions of the present invention may especially constitute hair styling/shaping, hair straightening, hair waving/curling, hair care, hair treatment, hair conditioning and hair shampoo products.

The compositions of the present invention can be provided in a plethora of galenic forms, including but not limited to creams, liquid, gel, cream-gel, lotion, foam, serum, paste, semi-solid, solid stick, stick-gel, or a powder, and may be in the form of a mousse or a spray, and may optionally be packaged as an aerosol, prepared according to the usual methods.

The following examples are intended to illustrate the invention without limiting the scope as a result. The percentages are given on a weight basis.

EXAMPLES

Example I

Based on the Wax Dispersion Protocol described above, aqueous wax dispersions were prepared/manufactured as follow:

A. Aqueous surfactant solution:
1. A surfactant mixture was prepared by adding gram amounts of nonionic surfactant(s) and ionic surfactant(s) in a container.
2. A preservative was added to the surfactant mixture.
3. Deionized water was added in an amount such that the final weight of the aqueous dispersion (including the weight of the wax) is 100 grams.
4. The surfactant solution was heated to about 75° C. in a water bath.

B. Oil: A weighed amount of the wax (e.g., beeswax or phyto olive wax) was heated and melted for a few minutes, e.g., about 5 minutes, in a microwave (or other appropriate heating device).

C. Emulsification process
1. While the aqueous surfactant solution was still at an elevated temperature (above room temperature, such as from about 65° C. to about 70° C.), the solution was mixed using a homogenizer/mixer (e.g., Silverson homogenizer) at a speed ranging from about 3000 to about 9000 rpm until bubbles were observed.
2. The melted hot wax was added to the surfactant solution close to the mixing head of the homogenizer while mixing.
3. Once all the wax was added, mixing was continued for at least 5 minutes.
4. The homogenizer blade was removed and the wax emulsion (dispersion) was mixed and cooled slightly towards room temperature before transferring into another container.
5. The dispersion was stored at room temperature.
6. The procedure above was followed for preparing other aqueous wax dispersions of the present invention using different waxes and/or surfactants at different levels.
7. The particle sizes of the solid wax particles were measured using image analysis (microscopy) and/or laser diffraction methods and/or by particle size analyzer to obtain an average particle size. For example, depending on the speed of mixing, solid wax particles of beeswax were found to have a particle size distribution ranging from 10 to 17 microns while solid wax particles of VP/eicosene copolymer were found to have a particle size distribution ranging from 1 to 11 microns, as measured by a Shimadzu SALD-7001 laser diffraction particle size analyzer, using quartz tubes having a refractive index of 1.2.

Table 1 Aqueous dispersions containing beeswax prepared according to the Wax Dispersion Protocol above

| Ingredient | Aqueous Dispersions % weight of ingredient | | | | |
|---|---|---|---|---|---|
| | A | B | C | D | E |
| Beeswax | 30 | 30 | 30 | 30 | 30 |
| PEG-30 glyceryl stearate (nonionic surfactant) | 2.5 | 1.25 | 2.7 | 1.25 | 2.5 |
| Monosodium stearoyl glutamate (anionic surfactant) | 0.5 | 0.25 | — | — | — |
| Disodium stearoyl glutamate (anionic surfactant) | — | — | 0.3 | 0.25 | — |
| Cetrimonium Chloride (cationic surfactant) | — | — | — | — | 0.5 |
| phenoxyethanol (preservative) | 0.5 | 0.5 | 0.5 | 0.5 | 0.5 |
| Deionized Water | Q.S. to 100 | Q.S. to 100 | Q.S. to 100 | Q.S. to 100 | Q.S. to 100 |
| Speed of mixing | 3000 | 4000 | 6000 | 6000 2-8 | 4000 |
| Solid wax particle size range by image analysis* (microns or µ) | 8-12 | 2-8 | 1-6 | 2-8 | 2-10 |
| Average wax particle size (microns or µ) | 10 | 6 | 5 | 6 | 8 |

*particle size is based on microscopic images of the wax dispersions in Table I and showed that aqueous dispersions of solid wax particles having different particle size ranges or distribution were obtained, depending on the amounts and/or types of surfactants used.

Example II: Table 2 Aqueous Dispersions Containing Phyto Olive Wax Prepared According to the Wax Dispersion Protocol Above

| Ingredient | Aqueous Dispersions % weight of ingredient | | | | | | | | | | |
|---|---|---|---|---|---|---|---|---|---|---|---|
| | F | G | H | I | J | K | L | M | N | O | P |
| AA | 30 | 30 | 30 | 30 | 30 | 30 | 30 | 25 | 20 | 20 | 25 |
| BB | 2.7 | 2.5 | 2.3 | 2.1 | 1.3 | 1.1 | 2.5 | 2.5 | 2.0 | 1.0 | 2.5 |
| CC | — | — | — | — | — | — | 0.5 | 0.5 | 0.5 | 0.25 | 0.5 |
| DD | 0.3 | 0.5 | 0.7 | 0.9 | 0.2 | 0.4 | 0.5 | 0.5 | 0.5 | 0.25 | 0.5 |
| EE | 0.5 | 0.5 | 0.5 | 0.5 | 0.5 | 0.5 | 0.5 | 0.5 | 0.5 | 0.5 | 0.5 |
| FF | Q.S. to 100 | Q.S. to 100 | Q.S. to 100 | Q.S. to 100 | Q.S. to 100 | Q.S. to 100 | Q.S. to 100 | Q.S. to 100 | Q.S. to 100 | Q.S. to 100 | Q.S. to 100 |

-continued

| Ingredient | Aqueous Dispersions % weight of ingredient | | | | | | | | | | |
|---|---|---|---|---|---|---|---|---|---|---|---|
| | F | G | H | I | J | K | L | M | N | O | P |
| GG | 3-15 | 2-15 | 2-10 | 3-12 | 1-12 | 1-20 | 2-10 | 2-10 | 1-8 | 1-8 | 2-10 |
| HH | 10 | 10 | 8 | 10 | 10 | 15 | 8 | 8 | 6 | 6 | 8 |

Details of the ingredients in above table:
AA = Phyto Olive wax (hydrogenated myristyl olive esters)
BB = PEG-30 glyceryl stearate (nonionic surfactant)
CC = Sorbitan palmitate (nonionic surfactant)
DD = Disodium stearoyl glutamate (anionic surfactant)
EE = Phenoxyethanol (preservative)
FF = Deionized Water
GG = Solid wax Particle size range by image analysis* (microns)
HH = Average wax particle size (microns)
*speed of mixing to make the dispersion was at 3000 rpm for all dispersions.

Microscopic images of the aqueous dispersions in Table III showed that aqueous dispersions of solid wax particles having different particle size ranges or distribution were obtained, depending on the amounts of the surfactants and/or wax and on the types of surfactants used.

Aqueous dispersions whose surfactant solution consisted of only the nonionic surfactant, e.g., PEG-30 glyceryl stearate, or in combination with another nonionic surfactant, e.g., sorbitan palmitate, were found to be unstable, that is, the wax particles agglomerated in the absence of an ionic surfactant in the dispersion.

Example III—Formulations Containing the Aqueous Dispersion

The formulations below (formulas 1 and 2) were prepared from an aqueous dispersion prepared according to the procedure described above and containing 30% beeswax, 2.7% of PEG-30 glyceryl stearate, 0.3% of disodium stearoyl glutamate and water (Q.S.) and adding an aliquot of the dispersion to each of the following: a gel-lotion/pump spray formulation (Formula 1 below) or to a mousse/foam formulation (Formula 2 below).

Note that the particle sizes of all formulas presented below were measured by image analysis from microscopic images of the dispersions.

Gel-Lotion/Pump Spray Formula 1 (Formulated as a Gel-Lotion or as a Non-Aerosol Spray)

| Ingredient | % weight |
|---|---|
| Beeswax Particles (average particle size 10 microns) | 5 |
| Polyacrylate-3 (23% active) | 2 |
| PEG-30 Glyceryl Stearate | 0.415 |
| Phenoxyethanol | 0.08 |
| Disodium Stearoyl Glutamate | 0.083 |
| Triethanolamine | 0.2 |
| Water | Q.S. to 100 |

Mousse or (Foam), Formula 2 (Aerosolized)

| Ingredient | % weight |
|---|---|
| Beeswax Particles (average particle size 10 microns) | 4.7 |
| Polyacrylate-3 (23% active) | 1.88 |
| PEG-30 Glyceryl Stearate | 0.390 |
| Phenoxyethanol | 0.0752 |
| Disodium Stearoyl Glutamate | 0.078 |
| Triethanolamine | 0.188 |
| A-70 propellant | 6 |
| Water | Q.S. to 100 |

Formulas 1 and 2 were tested on hair on the head of human subjects. After applying Formula 1 or Formula 2 with a comb or with the fingers onto dry or damp hair, the hair was heated using a blow drier after which the hair was styled/shaped as the temperature on the hair cooled down to room temperature. Upon cooling, it was observed that the formulas did not give a sticky or tacky feel to the hair. When more shaping and re-positioning of the hair was desired, the hair was heated again and the hair was re-positioned/re-shaped a different configuration without compromising the characteristics related to styling upon each application of heat the hair and without having to reapply the formulas onto the hair. Thus, it was possible to style the hair in several ways (e.g., helmet look, straightened curls, curling) using different curling/styling devices such as the flat iron or a comb without re-applying the formulas onto the hair. The formulas were easily removed from the hair with warm water and shampoo.

The aqueous dispersion can also be employed in a shampoo formulation as shown below.

Hair Care (Cleansing/Conditioning) Composition, Formula 3

| Ingredient | % weight |
|---|---|
| Beeswax Particles (average particle size 10 microns) | 5.0 |
| PEG-30 Glyceryl Stearate | 0.415 |
| Disodium Stearoyl Glutamate | 0.083 |
| Sodium laureth sulfate | 8.0 |
| Coco-betaine, Cocamide MIPA | 5.1 |
| Laureth-5 carboxylic acid | 0.7 |
| Silicone | 0.6 |
| Hexylene glycol, Propylene glycol | 0.9 |
| Polyquaternium-7 | 0.5 |
| PEG-55 propylene glycol oleate | 0.3 |
| PEG-60 Hydrogenated castor oil | 0.15 |
| preservatives, plant extracts, pH adjusters and Water | Q.S. to 100 |

The hair on the head of human subjects was shampooed with Formula 3 and rinsed. The hair was subsequently exposed to heat by blow drying. It was found that the hair could be shaped according to the desired style without having to apply any other styling or hair cosmetic composition onto the hair. It was also found that the formula provided a good curl hold/retention.

The following formulas demonstrate the use of other types of waxes comprising the solid wax particles of the aqueous dispersions of the present disclosure (formulas 4 to 6).

Hair Styling Composition Containing Phyto Olive Wax, Formula 4

| INCI Name | % by weight |
|---|---|
| POLYACRYLATE-3 | 0.46 |
| TRIETHANOLAMINE | 0.2 |
| PHENOXYETHANOL | 0.08 |
| SODIUM LAURYL SULFATE | 0.02 |
| HYDROGENATED MYRISTYL OLIVE ESTERS (phyto olive wax) (particle size range of 2-10 microns) | 5.0 |
| SORBITAN PALMITATE | 0.1 |
| DISODIUM STEAROYL GLUTAMATE | 0.1 |
| PEG-30 GLYCERYL STEARATE | 0.5 |
| WATER | Q.S. 100 |

Formula 4 above provided more shine and a sleek look to hair compared to a formula containing the beeswax aqueous dispersion (formula 1).

Hair Styling Composition Containing Ditrimethyloylpropane Tetrastearate Wax, Formula 5

| INCI Name | % by weight |
|---|---|
| POLYACRYLATE-3 | 0.46 |
| TRIETHANOLAMINE | 0.2 |
| PHENOXYETHANOL | 0.08 |
| SODIUM LAURYL SULFATE | 0.02 |
| DITRIMETHYLOLPROPANE TETRASTEARATE (particle size range of 5-20 microns) | 5.0 |
| DISODIUM STEAROYL GLUTAMATE | 0.083 |
| PEG-30 GLYCERYL STEARATE | 0.415 |
| WATER | Q.S. 100 |

Formula 5 above provided improved styleability to hair, a tighter curl hold, more shape memory, more body and a sleeker look to hair compared to a formula containing the beeswax aqueous dispersion (formula 1).

Hair Styling Composition Containing VP/Eicosene Polymer Wax, Formula 6

| INCI Name | % by weight |
|---|---|
| POLYACRYLATE-3 | 0.46 |
| TRIETHANOLAMINE | 0.2 |
| PHENOXYETHANOL | 0.08 |
| SODIUM LAURYL SULFATE | 0.02 |
| VP/EICOSENE COPOLYMER (particle size range of 2-8 microns) | 5.0 |
| DISODIUM STEAROYL GLUTAMATE | 0.083 |
| PEG-30 GLYCERYL STEARATE | 0.415 |
| WATER | Q.S. 100 |

Formula 6 above provided a tighter curl pattern to hair compared to a convention formula for curling or maintaining the curl of hair.

From the results observed from the use of the formulas above with respect to styling and shaping hair, it was found that different styling and shaping effects on the hair can be obtained, depending on the type of wax used in the aqueous dispersion.

Example IV—Comparative Example

The effect of styling hair with a formula containing an aqueous dispersion of beeswax prepared according to the procedure described above was compared to that of styling hair with a conventional wax formula for styling hair. The conventional wax formula was prepared using traditional methods of preparing a wax hair styling product wherein the wax is not pre-dispersed and is directly added to rest of the ingredients.

Gel Composition Containing a Beeswax Aqueous Dispersion, Formula 7

| INCI Name | % by weight |
|---|---|
| POLYACRYLATE-3 (in Viscophobe DB 1000) | 0.46 |
| TRIETHANOLAMINE | 0.2 |
| PHENOXYETHANOL | 0.08 |
| SODIUM LAURYL SULFATE | 0.02 |
| BEESWAX (particle size range of 8-10 microns) | 5.0 |
| SORBITAN PALMITATE | 0.1 |
| DISODIUM STEAROYL GLUTAMATE | 0.08 |
| PEG-30 GLYCERYL STEARATE | 0.4 |
| WATER | Q.S. 100 |

Conventional Wax Formula, Formula 8

| INCI Name | % by weight |
|---|---|
| BEESWAX | 10.0 |
| VA/VINYL BUTYL BENZOATE/CROTONATES COPOLYMER | 4.0 |
| ACRYLATES/C10-30 ALKYL ACRYLATE CROSSPOLYMER | 0.5 |
| TRIBEHENIN | 3.0 |
| NONIONIC SURFACTANTS (ALKOXYLATED FATTY ALCOHOLS) | 4.3 |
| FATTY ALCOHOL | 6.8 |
| GLYCERIN, PROPYLENE GLYCOL | 4 |
| CAPRYLIC/CAPRIC TRIGLYCERIDE, PEG-40 HYDROGENATED CASTOR OIL | 14.2 |
| PPG-2 MYRISTYL ETHER PROPIONATE, BIS-DIGLYCERYL POLYACYLADIPATE-2 | 7.4 |
| AMINOMETHYL PROPANOL | 0.92 |
| PRESERVATIVE, FRAGRANCE, SODIUM CHLORIDE, MAGNESIUM CHLORIDE, COLORANTS, HYDROLYZED WHEAT STARCH | 0.7 |
| WATER | Q.S. 100 |

When Formulas 7 and 8 were tested on the hair of human volunteers, formula 7 provided more root lift, volume, body and restyleability to the hair. Moreover, the hair dressers preferred formula 7 because it was less sticky on the hair, had a better feel on the hands, and provided better wettability to the hair.

It is to be understood that the foregoing describes preferred embodiments of the invention and that modifications may be made therein without departing from the spirit or scope of the invention as set forth in the claims.

What is claimed is:

1. A hair styling-composition comprising:
(a) from about 0.5% to about 20% by weight, based on the total weight of the composition, of an aqueous dispersion containing:
   (i) solid wax particles having a particle size ranging from about 5 microns to about 25 microns and comprising at least one wax chosen from beeswax, hydrogenated myristyl olive esters, hydrogenated stearyl olive esters, VP/eicosene copolymer, ditrimethyloylpropane tetrastearate and C30-45 alkyldimethylsilyl propylsilsesquioxane, and wherein the at least one wax is present in an amount of from about 20% to about 40% by weight, based on the total weight of the aqueous dispersion;
   (ii) from about 1.5% to about 3.0% by weight of a surfactant mixture comprising:
      from about 60% to about 95% by weight, based on the total weight of the surfactant mixture, of at least one nonionic surfactant chosen from PEG-30 glyceryl stearate, sorbitan palmitate and mixtures thereof; and
      from about 5% to about 20% by weight, based on the total weight of the surfactant mixture, of at least one cationic surfactant chosen from cetrimonium chloride, behentrimonium chloride, and mixtures thereof;
      wherein the surfactant mixture is free of amphoteric surfactants;
      wherein the average difference in the particle sizes of the solid wax particles is not more than about 20 microns;
   (iii) water; and
   (iv) an optional ingredient comprising at least one additional ingredient chosen from a wax having a melting point of 35° C. or less, oils, emulsifying polymers, sunscreen agents, pigments/dyes, silicas, talc, clays and perfumes;
(b) at least one cosmetically acceptable carrier; and
(c) optionally, at least one auxiliary agent.

2. A hair styling-composition comprising:
(a) from about 0.5% to about 20% by weight, based on the total weight of the composition, of an aqueous dispersion containing:
   (i) solid wax particles having a particle size ranging from about 5 microns to about 25 microns and comprising at least one wax chosen from beeswax, hydrogenated myristyl olive esters, hydrogenated stearyl olive esters, VP/eicosene copolymer, ditrimethyloylpropane tetrastearate and C30-45 alkyldimethylsilyl propylsilsesquioxane, and wherein the at least one wax is present in an amount of from about 20% to about 40% by weight, based on the total weight of the aqueous dispersion;
   (ii) from about 1.5% to about 3.0% by weight of a surfactant mixture comprising:
      from about 60% to about 95% by weight, based on the total weight of the surfactant mixture, of at least one nonionic surfactant chosen from PEG-30 glyceryl stearate, sorbitan palmitate and mixtures thereof; and
      from about 5% to about 20% by weight, based on the total weight of the surfactant mixture, of at least one anionic surfactant chosen from dipalmitoylethyl hydroxyethylmonium methosulfate, distearoylethyl hydroxyethylmonium methosulfate, disodium stearoyl glutamate and sodium stearoyl glutamate, and mixtures thereof;
      wherein the surfactant mixture is free of amphoteric surfactants;
   (iii) water; and
   (iv) an optional ingredient comprising at least one additional ingredient chosen from a wax having a melting point of 35° C. or less, oils, emulsifying polymers, sunscreen agents, pigments/dyes, silicas, talc, clays, and perfumes;
   wherein the average difference in the particle sizes of the solid wax particles is not more than about 20 microns;
(b) at least one cosmetically acceptable carrier; and
(c) optionally, at least one auxiliary agent.

3. A method of shaping hair, the method comprising:
(1) applying onto the hair, a hair styling composition comprising:
   (a) from about 0.5% to about 20% by weight, based on the total weight of the composition, of an aqueous dispersion comprising:
      (i) solid wax particles having a particle size ranging from about 5 microns to about 25 microns and comprising at least one wax chosen from beeswax, hydrogenated myristyl olive esters, hydrogenated stearyl olive esters, VP/eicosene copolymer, ditrimethyloylpropane tetrastearate and C30-45 alkyldimethylsilyl propylsilsesquioxane, and wherein the at least one wax is present in an amount of from about 20% to about 40% by weight, based on the total weight of the aqueous dispersion;
      (ii) from about 1.5% to about 3.0% by weight of a surfactant mixture comprising:
         from about 60% to about 95% by weight, based on the total weight of the surfactant mixture, of at least one nonionic surfactant chosen from PEG-30 glyceryl stearate, sorbitan palmitate and mixtures thereof; and
         from about 5% to about 20% by weight, based on the total weight of the surfactant mixture, of at least one cationic surfactant chosen from cetrimonium chloride, behentrimonium chloride, and mixtures thereof;
         wherein the surfactant mixture is free of amphoteric surfactants;
      (iii) water; and
      (iv) an optional ingredient comprising at least one additional ingredient chosen from a wax having a melting point of 35° C. or less, oils, emulsifying polymers, sunscreen agents, pigments/dyes, silicas, talc, clays and perfumes;
      wherein the average difference in the particle sizes of the solid wax particles is not more than about 20 microns;
   (b) at least one cosmetically acceptable carrier; and
   (c) optionally, at least one auxiliary agent; and
(2) heating the hair in order to melt the solid wax particles.

4. The composition of claim 1, wherein (a)(i) is of a spherical, ellipsoidal or oval shape.

5. The composition of claim 1, wherein (b) is chosen from water, volatile organic solvents, non-volatile organic solvents, silicones, polyols, glycols, glycol ethers, oils, and mixtures thereof.

6. The composition of claim 1, wherein the at least one auxiliary agent is chosen from liquid lipids, film forming polymers, rheology modifiers, humectants and moisturizing agents, emulsifying agents, structuring agents, propellants, surfactants, shine agents, conditioning agents, cosmetically, dermatologically and pharmaceutically active agents, vitamins, and plant extracts.

7. The composition of claim 1, wherein the composition further comprises at least one rheology modifier chosen from acrylate- or acrylic-based polymers and cellulose-based thickening agents.

8. The composition of claim 1, wherein the composition further comprises a volatile organic solvent.

9. The composition of claim 1, wherein the composition further comprises a propellant.

10. The composition of claim 1, wherein the solid wax particles are heat-activated.

11. The method of claim 3, wherein the solid wax particles are of a spherical, ellipsoidal or oval shape.

12. The method of claim 3, wherein the cosmetically acceptable carrier is chosen from water, volatile organic solvents, non-volatile organic solvents, silicones, polyols, glycols, glycol ethers, oils, and mixtures thereof.

13. The method of claim 3, wherein the at least one auxiliary agent is chosen from liquid lipids, film forming polymers, rheology modifiers, humectants and moisturizing agents, propellants, surfactants, shine agents, emulsifying agents, structuring agents, conditioning agents, cosmetically, dermatologically and pharmaceutically active agents, vitamins, and plant extracts.

14. The method of claim 3, wherein the composition further comprises at least one film forming polymer chosen from acrylate- or acrylic-based polymers and cellulose-based thickening agents.

15. The method of claim 3, wherein the composition further comprises a volatile organic solvent.

16. The method of claim 3, wherein the composition further comprises a propellant.

17. A method of shaping hair, the method comprising:
(1) applying onto the hair, a hair styling composition comprising:
(a) from about 0.5% to about 20% by weight, based on the total weight of the composition, of an aqueous dispersion containing:
(i) solid wax particles having a particle size ranging from about 5 microns to about 25 microns and comprising at least one wax chosen from beeswax, hydrogenated myristyl olive esters, hydrogenated stearyl olive esters, VP/eicosene copolymer, ditrimethyloylpropane tetrastearate and C30-45 alkyldimethylsilyl propylsilsesquioxane, and wherein the at least one wax is present in an amount of from about 20% to about 40% by weight, based on the total weight of the aqueous dispersion;
(ii) from about 1.5% to about 3.0% by weight of a surfactant mixture comprising:
from about 60% to about 95% by weight, based on the total weight of the surfactant mixture, of at least one nonionic surfactant chosen from PEG-30 glyceryl stearate, sorbitan palmitate and mixtures thereof; and
from about 5% to about 20% by weight, based on the total weight of the surfactant mixture, of at least one anionic surfactant chosen from dipalmitoylethyl hydroxyethylmonium methosulfate, distearoylethyl hydroxyethylmonium methosulfate, disodium stearoyl glutamate and sodium stearoyl glutamate, and mixtures thereof;
wherein the surfactant mixture is free of amphoteric surfactants;
(iii) water; and
(iv) an optional ingredient comprising at least one additional ingredient chosen from a wax having a melting point of 35° C. or less, oils, emulsifying polymers, sunscreen agents, pigments/dyes, silicas, talc, clays, and perfumes;
wherein the average difference in the particle sizes of the solid wax particles is not more than about 20 microns;
(b) at least one cosmetically acceptable carrier; and
(c) optionally, at least one auxiliary agent; and
(2) heating the hair in order to melt the solid wax particles.

18. The method of claim 17, wherein the solid wax particles are of a spherical, ellipsoidal or oval shape.

19. The method of claim 17, wherein the cosmetically acceptable carrier is chosen from water, volatile organic solvents, non-volatile organic solvents, silicones, polyols, glycols, glycol ethers, oils, and mixtures thereof.

20. The method of claim 17, wherein the at least one auxiliary agent is chosen from liquid lipids, film forming polymers, rheology modifiers, humectants and moisturizing agents, propellants, surfactants, shine agents, emulsifying agents, structuring agents, conditioning agents, cosmetically, dermatologically and pharmaceutically active agents, vitamins, and plant extracts.

21. The method of claim 17, wherein the composition further comprises at least one film forming polymer chosen from acrylate- or acrylic-based polymers and cellulose-based thickening agents.

22. The method of claim 17, wherein the composition further comprises a volatile organic solvent.

23. The method of claim 17, wherein the composition further comprises a propellant.

24. The composition of claim 2, wherein (a)(i) is of a spherical, ellipsoidal or oval shape.

25. The composition of claim 2, wherein (b) is chosen from water, volatile organic solvents, non-volatile organic solvents, silicones, polyols, glycols, glycol ethers, oils, and mixtures thereof.

26. The composition of claim 2, wherein the at least one auxiliary agent is chosen from liquid lipids, film forming polymers, rheology modifiers, humectants and moisturizing agents, emulsifying agents, structuring agents, propellants, surfactants, shine agents, conditioning agents, cosmetically, dermatologically and pharmaceutically active agents, vitamins, and plant extracts.

27. The composition of claim 2, wherein the composition further comprises at least one rheology modifier chosen from acrylate- or acrylic-based polymers and cellulose-based thickening agents.

28. The composition of claim 2, wherein the composition further comprises a volatile organic solvent.

29. The composition of claim 2, wherein the composition further comprises a propellant.

30. The composition of claim 2, wherein the solid wax particles are heat-activated.

* * * * *